United States Patent
Rahmanzadeh et al.

(10) Patent No.: US 11,802,927 B2
(45) Date of Patent: Oct. 31, 2023

(54) SYSTEM AND METHOD OF MAGNETIC RESONANCE IMAGING METHOD FOR MONITORING REMYELINATION

(71) Applicants: Cornell University, Ithaca, NY (US); Universität Basel, Basel (CH)

(72) Inventors: Reza Rahmanzadeh, Basel (CH); Cristina Granziera, Binningen (CH); Yi Wang, New York, NY (US); Riccardo Galbusera, Freiburg im Breisgau (DE)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/687,392

(22) Filed: Mar. 4, 2022

(65) Prior Publication Data
US 2022/0283256 A1    Sep. 8, 2022

Related U.S. Application Data

(60) Provisional application No. 63/156,802, filed on Mar. 4, 2021.

(51) Int. Cl.
  *G01R 33/565* (2006.01)
  *A61B 5/055* (2006.01)
  (Continued)

(52) U.S. Cl.
  CPC ........ *G01R 33/56536* (2013.01); *A61B 5/055* (2013.01); *G01R 33/50* (2013.01); *G01R 33/5608* (2013.01)

(58) Field of Classification Search
  CPC .............. G01R 33/56536; G01R 33/50; G01R 33/5608; A61B 5/055
  See application file for complete search history.

(56) References Cited

U.S. PATENT DOCUMENTS

| | | | |
|---|---|---|---|
| 8,886,283 B1* | 11/2014 | Chen .................... | A61B 5/4064 382/128 |
| 2011/0044524 A1* | 2/2011 | Wang ................. | G01R 33/5601 382/131 |

(Continued)

OTHER PUBLICATIONS

Wang Y, Spincemaille P, Liu Z, et al. Clinical quantitative susceptibility mapping (QSM): Biometal imaging and its emerging roles in patient care. J Magn Reson Imaging. Oct. 2017;46(4):951-971. doi:10.1002/jmri.25693.

(Continued)

*Primary Examiner* — Dixomara Vargas
(74) *Attorney, Agent, or Firm* — Leydig, Voit & Mayer, Ltd.

(57) ABSTRACT

Quantitative susceptibility mapping methods, systems and computer-accessible medium include generating images of tissue magnetism property from complex magnetic resonance imaging data using the Bayesian inference approach. The tissue magnetism images is then used to monitor remyelination, such as remyelination in multiple sclerosis patients in response to therapy. Multiple sclerosis lesions defined on magnetic resonance imaging are further characterized on tissue magnetism images into hyperintense, isointense and hypointense parts for measuring remyelination. Thus, magnetic susceptibility information and other tissue properties associated with at least one structure are determined.

20 Claims, 27 Drawing Sheets

(51) Int. Cl.
*G01R 33/56* (2006.01)
*G01R 33/50* (2006.01)

(56) References Cited

U.S. PATENT DOCUMENTS

| | | | | |
|---|---|---|---|---|
| 2012/0321162 | A1* | 12/2012 | Liu | G01R 33/5616 382/131 |
| 2013/0221961 | A1* | 8/2013 | Liu | G01R 33/56545 324/307 |
| 2015/0002148 | A1* | 1/2015 | Liu | A61B 5/055 324/309 |
| 2015/0145515 | A1* | 5/2015 | Liu | G01R 33/243 324/309 |
| 2016/0252597 | A1* | 9/2016 | Liu | G01R 33/5608 324/309 |
| 2018/0180688 | A1* | 6/2018 | Koch | G01R 33/5616 |
| 2018/0321347 | A1* | 11/2018 | Wang | G01R 33/5608 |

OTHER PUBLICATIONS

Bagnato F, Hametner S, Yao B, et al. Tracking iron in multiple sclerosis: a combined imaging and histopathological study at 7 Tesla. Brain. Dec. 2011;134(Pt 12):3602-15. doi:10.1093/brain/awr278.

Dal-Bianco A, Grabner G, Kronnerwetter C, et al. Slow expansion of multiple sclerosis iron rim lesions: pathology and 7 T magnetic resonance imaging. Acta Neuropathol. Jan. 2017;133(1):25-42. doi:10.1007/s00401-016-1636-z.

Stephenson E, Nathoo N, Mahjoub Y, Dunn JF, Yong VW. Iron in multiple sclerosis: roles in neurodegeneration and repair. Nat Rev Neurol. Aug. 2014;10(8):459-68. doi:10.1038/nrneurol.2014.118.

Chen W, Gauthier SA, Gupta A, et al. Quantitative susceptibility mapping of multiple sclerosis lesions at various ages. Radiology. Apr. 2014;271(1):183-92. doi:10.1148/radiol.13130353.

Lassmann H. Multiple Sclerosis Pathology. Cold Spring Harb Perspect Med. Mar. 1, 2018;8(3)doi:10.1101/cshperspect.a028936.

Kuhlmann T, Ludwin S, Prat A, Antel J, Bruck W, Lassmann H. An updated histological classification system for multiple sclerosis lesions. Acta Neuropathol. Jan. 2017;133(1):13-24. doi:10.1007/s00401-016-1653-y.

Patrikios P, Stadelmann C, Kutzelnigg A, et al. Remyelination is extensive in a subset of multiple sclerosis patients. Brain. Dec. 2006;129(Pt 12):3165-72. doi:10.1093/brain/awl217.

Goldschmidt T, Antel J, Konig FB, Bruck W, Kuhlmann T. Remyelination capacity of the MS brain decreases with disease chronicity. Neurology. Jun. 2, 2009;72(22):1914-21. doi:10.1212/WNL.0b013e3181a8260a.

Kuhlmann T, Miron V, Cui Q, Wegner C, Antel J, Bruck W. Differentiation block of oligodendroglial progenitor cells as a cause for remyelination failure in chronic multiple sclerosis. Brain. Jul. 2008;131(Pt 7):1749-58. doi:10.1093/brain/awn096.

Lassmann H, van Horssen J, Mahad D. Progressive multiple sclerosis: pathology and pathogenesis. Nat Rev Neurol. Nov. 5, 2012;8(11):647-56. doi:10.1038/nrneurol.2012.168.

Kuhlmann T, Lingfeld G, Bitsch A, Schuchardt J, Bruck W. Acute axonal damage in multiple sclerosis is most extensive in early disease stages and decreases over time. Brain. Oct. 2002;125(Pt 10):2202-12. doi:10.1093/brain/awf235.

Friese MA, Schattling B, Fugger L. Mechanisms of neurodegeneration and axonal dysfunction in multiple sclerosis. Nat Rev Neurol. Apr. 2014;10(4):225-38. doi:10.1038/nrneurol.2014.37.

Tham M, Frischer JM, Weigand SD, et al. Iron Heterogeneity in Early Active Multiple Sclerosis Lesions. Ann Neurol. Nov. 27, 2020;doi:10.1002/ana.25974.

Popescu BF, Frischer JM, Webb SM, et al. Pathogenic implications of distinct patterns of iron and zinc in chronic MS lesions. Acta Neuropathol. Jul. 2017;134(1):45-64. doi:10.1007/s00401-017-1696-8.

Laule C, Moore GRW. Myelin water imaging to detect demyelination and remyelination and its validation in pathology. Brain Pathol. Sep. 2018;28(5):750-764. doi:10.1111/bpa.12645.

Nguyen TD, Deh K, Monohan E, et al. Feasibility and reproducibility of whole brain myelin water mapping in 4 minutes using fast acquisition with spiral trajectory and adiabatic T2prep (FAST-T2) at 3T. Magn Reson Med. Aug. 2016;76 (2):456-65. doi:10.1002/mrm.25877.

Cercignani M, Gandini Wheeler-Kingshott C. From micro- to macro-structures in multiple sclerosis: what is the added value of diffusion imaging. NMR Biomed. Apr. 2019;32(4):e3888. doi:10.1002/nbm.3888.

Moore GR, Leung E, MacKay AL, et al. A pathology-MRI study of the short-T2 component in formalin-fixed multiple sclerosis brain. Neurology. Nov. 28, 2000;55(10):1506-10. doi:10.1212/wnl.55.10.1506 (Abstract).

Kozlowski P, Rosicka P, Liu J, Yung AC, Tetzlaff W. In vivo longitudinal Myelin Water Imaging in rat spinal cord following dorsal column transection injury. Magn Reson Imaging. Apr. 2014;32(3):250-8. doi:10.1016/j.mri.2013.12.006.

Kaden E, Kelm ND, Carson RP, Does MD, Alexander DC. Multi-compartment microscopic diffusion imaging. Neuroimage. Oct. 1, 2016;139:346-359. doi:10.1016/j.neuroimage.2016.06.002.

Bagnato F, Franco G, Thomas N, Smith S, Dortch R, Xu J. Multi-compartment Spherical Microscopic Diffusion Imaging Using Spherical Mean Techniques to Probe Axonal Injury in Multiple Sclerosis. Neurology. 2018:P3. 383.

Grussu F, Schneider T, Tur C, et al. Neurite dispersion: a new marker of multiple sclerosis spinal cord pathology? Ann Clin Transl Neurol. Sep. 2017;4(9):663-679. doi:10.1002/acn3.445.

Colgan N, Siow B, O'Callaghan JM, et al. Application of neurite orientation dispersion and density imaging (NODDI) to a tau pathology model of Alzheimer's disease. Neuroimage. Jan. 15, 2016;125:739-744. doi:10.1016/j.neuroimage.2015.10.043.

Thompson AJ, Banwell BL, Barkhof F, et al. Diagnosis of multiple sclerosis: 2017 revisions of the McDonald criteria. Lancet Neurol. Feb. 2018;17(2):162-173. doi:10.1016/S1474-4422(17)30470-2.

Lublin FD, Reingold SC, Cohen JA, et al. Defining the clinical course of multiple sclerosis: the 2013 revisions. Neurology. Jul. 15, 2014;83(3):278-86. doi:10.1212/WNL.0000000000000560.

Veraart J, Novikov DS, Christiaens D, Ades-Aron B, Sijbers J, Fieremans E. Denoising of diffusion MRI using random matrix theory. Neuroimage. Nov. 15, 2016;142:394-406. doi:10.1016/j.neuroimage.2016.08.016.

Andersson JLR, Sotiropoulos SN. An integrated approach to correction for off-resonance effects and subject movement in diffusion MR imaging. Neuroimage. Jan. 15, 2016;125:1063-1078. doi:10.1016/j.neuroimage.2015.10.019.

Liu T, Xu W, Spincemaille P, Avestimehr AS, Wang Y. Accuracy of the morphology enabled dipole inversion (MEDI) algorithm for quantitative susceptibility mapping in MRI. IEEE Trans Med Imaging. Mar. 2012;31(3):816-24. doi:10.1109/TMI.2011.2182523.

Absinta M, Nair G, Filippi M, et al. Postmortem magnetic resonance imaging to guide the pathologic cut: individualized, 3-dimensionally printed cutting boxes for fixed brains. J Neuropathol Exp Neurol. Aug. 2014;73(8):780-8. doi:10.1097/NEN.0000000000000096.

Yushkevich PA, Piven J, Hazlett HC, et al. User-guided 3D active contour segmentation of anatomical structures: significantly improved efficiency and reliability. Neuroimage. Jul. 1, 2006;31(3):1116-28. doi:10.1016/j.neuroimage.2006.01.015.

Allan C, Burel JM, Moore J, et al. OMERO: flexible, model-driven data management for experimental biology. Nat Methods. Feb. 28, 2012;9(3):245-53. doi:10.1038/nmeth.1896.

La Rosa F, Abdulkadir A, Fartaria MJ, et al. Multiple sclerosis cortical and WM lesion segmentation at 3T MRI: a deep learning method based on FLAIR and MP2RAGE. Neuroimage Clin. Jun. 30, 2020;27:102335. doi:10.1016/j.nicl.2020.102335.

Jenkinson M, Beckmann CF, Behrens TE, Woolrich MW, Smith SM. Fsl. Neuroimage. Aug. 15, 2012;62(2):782-90. doi:10.1016/j.neuroimage.2011.09.015.

(56) References Cited

OTHER PUBLICATIONS

Rahmanzadeh R, Lu PJ, Barakovic M, et al. Myelin and axon pathology in multiple sclerosis assessed by myelin water and multi-shell diffusion imaging. Brain. Mar. 9, 2021;doi:10.1093/brain/awab088.

Fischl B. FreeSurfer. Neuroimage. Aug. 15, 2012;62(2):774-81. doi:10.1016/j.neuroimage.2012.01.021.

Absinta M, Sati P, Schindler M, et al. Persistent 7-tesla phase rim predicts poor outcome in new multiple sclerosis patient lesions. Journal of Clinical Investigation. Jul. 2016;126(7):2597-2609. doi:10.1172/Jci86198.

Dal-Bianco A, Grabner G, Kronnerwetter C, et al. Slow expansion of multiple sclerosis iron rim lesions: pathology and 7 T magnetic resonance imaging. Acta Neuropathologica. Jan. 2017;133(1):25-42. doi:10.1007/s00401-016-1636-z.

Hametner S, Wimmer I, Haider L, Pfeifenbring S, Bruck W, Lassmann H. Iron and neurodegeneration in the multiple sclerosis brain. Ann Neurol. Dec. 2013;74(6):848-61. doi:10.1002/ana.23974.

Harrison DM, Li X, Liu H, et al. Lesion Heterogeneity on High-Field Susceptibility MRI Is Associated with Multiple Sclerosis Severity. AJNR Am J Neuroradiol. Aug. 2016;37(8):1447-53. doi:10.3174/ajnr.A4726.

Wisnieff C, Ramanan S, Olesik J, Gauthier S, Wang Y, Pitt D. Quantitative susceptibility mapping (QSM) of white matter multiple sclerosis lesions: Interpreting positive susceptibility and the presence of iron. Magn Reson Med. Aug. 2015;74(2):564-70. doi:10.1002/mrm.25420.

Bian W, Tranvinh E, Tourdias T, et al. In Vivo 7T MR Quantitative Susceptibility Mapping Reveals Opposite Susceptibility Contrast between Cortical and White Matter Lesions in Multiple Sclerosis. AJNR Am J Neuroradiol. Oct. 2016;37(10):1808-1815. doi:10.3174/ajnr.A4830.

Ropele S, Enzinger C, Fazekas F. Iron Mapping in Multiple Sclerosis. Neuroimaging Clin N Am. May 2017;27 (2):335-342. doi:10.1016/j.nic.2016.12.003.

Li W, Wu B, Liu C. Quantitative susceptibility mapping of human brain reflects spatial variation in tissue composition. Neuroimage. Apr. 15, 2011;55(4):1645-56. doi:10.1016/j.neuroimage.2010.11.088.

Deh K, Ponath GD, Molvi Z, et al. Magnetic susceptibility increases as diamagnetic molecules breakdown: Myelin digestion during multiple sclerosis lesion formation contributes to increase on QSM. J Magn Reson Imaging. Nov. 2018;48(5):1281-1287. doi:10.1002/jmri.25997.

Yao B, Bagnato F, Matsuura E, et al. Chronic multiple sclerosis lesions: characterization with high-field-strength MR imaging. Radiology. Jan. 2012;262(1):206-15. doi:10.1148/radiol.11110601.

Adamczyk B, Adamczyk-Sowa M. New Insights into the Role of Oxidative Stress Mechanisms in the Pathophysiology and Treatment of Multiple Sclerosis. Oxid Med Cell Longev. 2016;2016:1973834. doi:10.1155/2016/1973834.

Haider L. Inflammation, Iron, Energy Failure, and Oxidative Stress in the Pathogenesis of Multiple Sclerosis. Oxid Med Cell Longev. 2015;2015:725370. doi:10.1155/2015/725370.

Kaunzner UW, Kang Y, Zhang S, et al. Quantitative susceptibility mapping identifies inflammation in a subset of chronic multiple sclerosis lesions. Brain. Jan. 1, 2019;142(1):133-145. doi:10.1093/brain/awy296.

Li X, Harrison DM, Liu H, et al. Magnetic susceptibility contrast variations in multiple sclerosis lesions. J Magn Reson Imaging. Feb. 2016;43(2):463-73. doi:10.1002/jmri.24976.

Todorich B, Pasquini JM, Garcia CI, Paez PM, Connor JR. Oligodendrocytes and myelination: the role of iron. Glia. Apr. 1, 2009;57(5):467-78. doi:10.1002/glia.20784.

Lubetzki C, Zalc B, Williams A, Stadelmann C, Stankoff B. Remyelination in multiple sclerosis: from basic science to clinical translation. Lancet Neurol. Aug. 2020;19(8):678-688. doi:10.1016/S1474-4422(20)30140-X.

Lee J, Nam Y, Choi JY, Kim EY, Oh SH, Kim DH. Mechanisms of T2 * anisotropy and gradient echo myelin water imaging. NMR Biomed. Apr. 2017;30(4)doi:10.1002/nbm.3513.

Kirilina E, Helbling S, Morawski M, et al. Superficial white matter imaging: Contrast mechanisms and whole-brain in vivo mapping. Sci Adv. Oct. 2020;6(41)doi:10.1126/sciadv.aaz9281.

Schultz V, van der Meer F, Wrzos C, et al. Acutely damaged axons are remyelinated in multiple sclerosis and experimental models of demyelination. Glia. Aug. 2017;65(8):1350-1360. doi:10.1002/glia.23167.

Kornek B, Storch MK, Weissert R, et al. Multiple sclerosis and chronic autoimmune encephalomyelitis: a comparative quantitative study of axonal injury in active, inactive, and remyelinated lesions. Am J Pathol. Jul. 2000;157(1):267-76. doi:10.1016/S0002-9440(10)64537-3.

Lee NJ, Ha SK, Sati P, et al. Potential role of iron in repair of inflammatory demyelinating lesions. J Clin Invest. Oct. 1, 2019;129(10):4365-4376. doi:10.1172/JCI126809.

Magliozzi R, Howell O, Vora A, et al. Meningeal B-cell follicles in secondary progressive multiple sclerosis associate with early onset of disease and severe cortical pathology. Brain. Apr. 2007;130(Pt 4):1089-104. doi:10.1093/brain/awm038.

Winges KM, Gilden DH, Bennett JL, Yu X, Ritchie AM, Owens GP. Analysis of multiple sclerosis cerebrospinal fluid reveals a continuum of clonally related antibody-secreting cells that are predominantly plasma blasts. J. Neuroimmunol. Dec. 2007;192(1-2):226-34. doi:10.1016/j.jneuroim.2007.10.009.

Patani R, Balaratnam M, Vora A, Reynolds R. Remyelination can be extensive in multiple sclerosis despite a long disease course. Neuropathol Appl Neurobiol. Jun. 2007;33(3):277-87. doi:10.1111/j.1365-2990.2007.00805.x.

Antel J, Antel S, Caramanos Z, Arnold DL, Kuhlmann T. Primary progressive multiple sclerosis: part of the MS disease spectrum or separate disease entity? Acta Neuropathol. May 2012;123(5):627-38. doi:10.1007/s00401-012-0953-0.

* cited by examiner

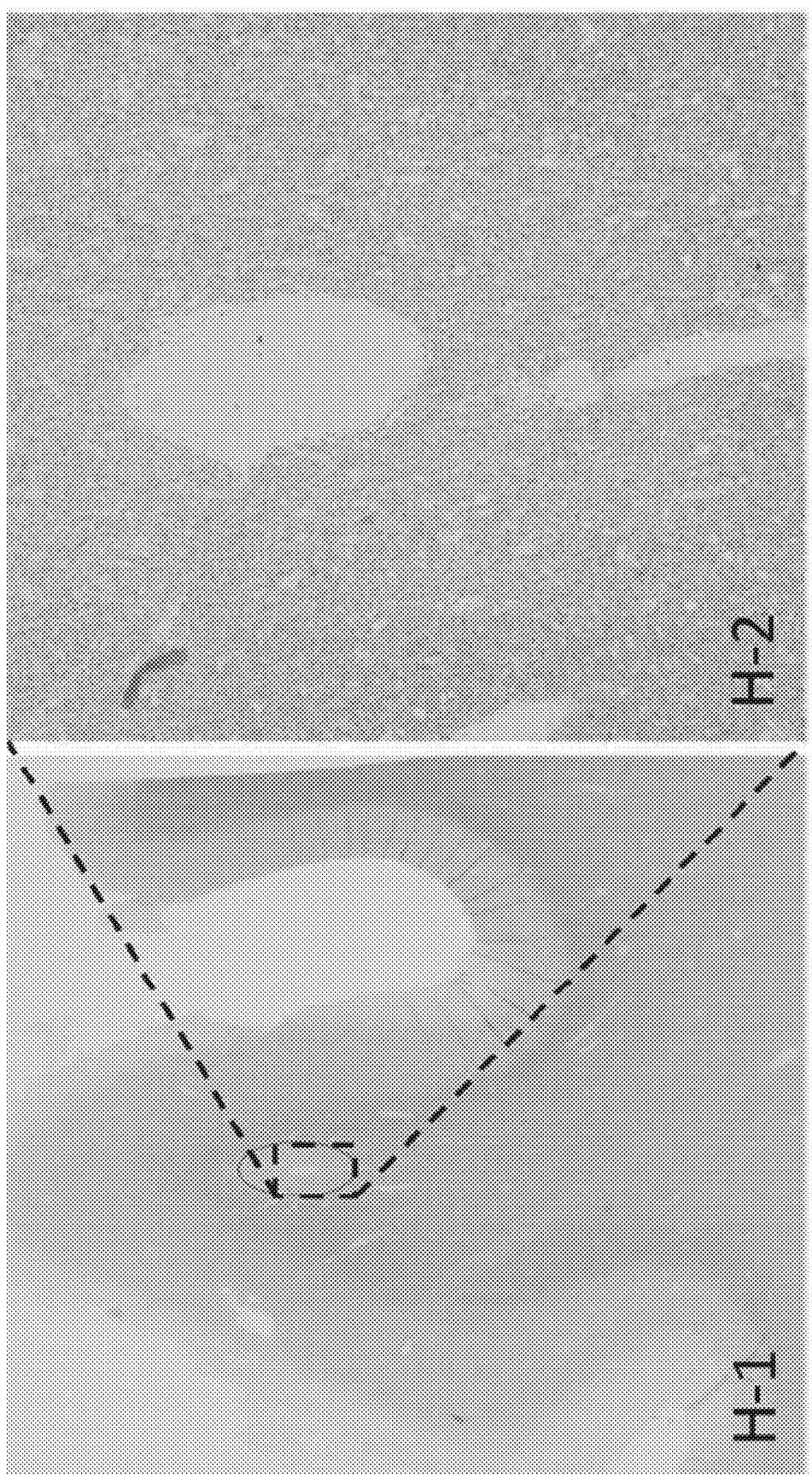

SYSTEM AND METHOD OF MAGNETIC RESONANCE IMAGING METHOD FOR MONITORING REMYELINATION

CROSS REFERENCE TO RELATED APPLICATIONS

This application claims priority to U.S. Provisional Patent Application No. 63/156,802, filed on Mar. 4, 2021, the disclosure of which is hereby incorporated by reference in its entirety.

TECHNICAL FIELD

This disclosure relates to magnetic resonance imaging, and more particularly to monitoring remyelination using signals collected in magnetic resonance imaging.

BACKGROUND

Quantitative susceptibility mapping (QSM) in magnetic resonance imaging (MM) has received increasing clinical and scientific interest. QSM is useful for characterizing and quantifying magnetic chemical compositions such as iron and myelin in brain tissue. Tissue composition of these compounds may be altered in various neurological disorders, such as multiple sclerosis. QSM is able to unravel novel information related to the magnetic susceptibility (or simply referred as susceptibility), a physical property of underlying tissue that depends on magnetic chemical compositions. Due to the prevalence of iron and myelin in brain tissue and their active involvement in brain functions, QSM is in general very useful for studying neurological disorders. Therefore, accurate mapping of the magnetic susceptibility induced by iron, myelin and other magnetic sources will provide tremendous benefit to clinical researchers to probe the structure and functions of human body, and to clinicians to better diagnose various diseases and provide relevant treatment.

The gradient echo (GRE) sequence is widely accessible and commonly used to acquire data for QSM. GRE can be acquired using Cartesian sampling with one or many lines in k-space sampled per TR, which is known as standard gradient echo imaging or echo planar imaging. GRE data comprise magnitude information with T2* contrast and phase information. QSM reconstruction can be performed using the approach of estimating the magnetic field from all echo signals of the GRE data before the field to magnetic susceptibility inversion. In general, magnetic susceptibility affects the complex MRI signal in a nonlinear manner. The corresponding inverse problems of nonlinear signal models are challengingly nonconvex.

MRI has been used to monitor multiple sclerosis (MS) patients. Conventional MRI, including T1 weighted imaging before and post gadolinium injection and T2 weighted imaging with and without fluid attenuated inversion recovery (FLAIR), are used to identify MS lesion size, location, and their dissemination in space and time. However, conventional MRI has difficulty in sensitizing MS disease activities and brain tissue therapeutic responses behind the sealed blood brain barrier, including ongoing chronic active inflammation and potential remyelination response to therapy. QSM has been developed and applied for monitoring chronic active inflammation in MS. Monitoring remyelination in response to therapy remains a challenge and an unmet medical need.

SUMMARY

Implementations of systems and methods for collecting and processing multiecho (including the single echo as a special case, including acquisition using cartesian, radial, spiral and other trajectories in k-space, including many k-space lines per TR or echo planar imaging) complex MM signals of a subject, and reconstructing maps of physical properties intrinsic to the subject (e.g., magnetic susceptibility) are described below. In some implementations, MR signal data corresponding to a subject can be transformed into susceptibility-based images that quantitatively depict the structure and/or composition and/or function of the subject. Using this quantitative susceptibility map, one or more susceptibility-based images of the subject can be generated and displayed to a user. The user can then use these images for diagnostic or experimental purposes, for example to investigate the structure and/or composition and/or function of the subject, and/or to diagnose and/or treat various conditions or diseases based, at least in part, on the images. As one or more of the described implementations can result in susceptibility-based images having higher quality and/or accuracy compared to other susceptibility mapping techniques, at least some of these implementations can be used to improve a user's understanding of a subject's structure and/or composition and/or function, and can be used to improve the accuracy of any resulting medical diagnoses or experimental analyses.

Exemplary implementations described below for the magnetic dipole inversion using incorporation of multiecho complex data based cost function, preconditioning, deep neural network, and enforcement of regional susceptibility contrasts improve susceptibility map quality including suppression of artificial signal variation in regions of low susceptibility contrasts and provide accurate susceptibility values with precise fidelity to the acquired multiecho complex Mill data, thereby ensuring quantification accuracy, experimental repeatability and reproducibility.

One aspect of this disclosure enables an accurate quantification of tissue magnetic susceptibility by the use of receiving multiecho complex magnetic resonance imaging data obtained by a magnetic resonance scanner, wherein the multiecho data at each echo time is complex and comprises magnitude and phase information or real and imaginary information regarding an object; and by the use of estimating a magnetic susceptibility distribution of the object based on the multiecho complex data at each echo time, wherein estimating the magnetic susceptibility distribution of the subject comprises determining a cost function, the cost function relating at least a data fidelity term involving a comparison between the measured and a susceptibility modeled complex signal at each echo time wherein the susceptibility modeled complex signal has time dependence in both signal magnitude and phase, and a regularization term associated with a structure prior information, and determining a magnetic susceptibility distribution based on minimizing the cost function Another aspect of the disclosure for estimating the magnetic susceptibility distribution includes identifying regions distributed over the whole image volume that have low susceptibility contrast according to a characteristic feature and adding a second regularization term associated with penalizing susceptibility variations in these regions. This regularization over low contrast regions allows for estimation and reduction of shadowing and/or streaking artifacts in these regions.

Another aspect of the disclosure for estimating the magnetic susceptibility distribution includes using a characteristic feature characterized by R2* value. The region of interest is determined by similar R2* properties of contiguous voxels; and the penalty of the second regularization term depends on a representative R2* value in the region of interest.

In some implementations, the object comprises a cortex, a putamen, a globus pallidus, a red nucleus, a substantia nigra, or a subthalamic nucleus of a brain, or a liver in an abdomen, and generating one or more images of the object comprises generating one or more images depicting the cortex, the putamen, the globus pallidus, the red nucleus, the substantia nigra, or the subthalamic nucleus of the brain.

In some implementations, the object comprises at least one of a multiple sclerosis lesion, and generating one or more images of the object comprises generating one or more images depicting at least one of the multiple sclerosis lesion. The multiple sclerosis lesion is segmented on T2 weighted imaging. The T2 region of the lesion is partitioned into hyperintense, isointense and hypointense subregions by comparing the magnetic susceptibility distribution in the T2 region of the lesion with the magnetic susceptibility distribution in a region surrounding the T2 region of the lesion.

The details of one or more embodiments are set forth in the accompanying drawings and the description below. Other features and advantages will be apparent from the description and drawings, and from the claims.

BRIEF DESCRIPTION OF THE DRAWINGS

FIG. 1A shows average QSM in WMLs, NAWM and WM-HC. FIG. 1B shows lesion-wise relative susceptibility of WMLs compared to peri-plaque white matter (PPWM).

FIGS. 3A-3L show remyelinated, chronic inactive and chronic active lesions in post-mortem QSM: A) remyelinated areas in lesion borders (myelin based protein (MBP) staining, A-1) appeared isointense in QSM (A-2), B) remyelinated lesions (shadow plaque; MBP staining, B-1) appeared hypointense in QSM with hyperintense traversing vessels (B-2), C) two remyelinated areas in lesions border (MBP staining, C-1): the periventricular one appeared isointense in QSM and the other one hyperintense relative to peri-plaque WM and hypointense relative to lesion center (C-2). D) remyelinated lesion (shadow plaque; MBP staining, D-1) appeared hypointense in QSM (D-2). E,G) microglia/macrophages (MBP-CR3/43 staining) and myelinating oligodendrocytes (BCAS1 staining; BCAS1+ oligodendrocytes are shown with blue arrows) are present in remyelinated areas of higher signal intensity in lesion C. F,H) lack of microglia/macrophages (MBP-CR3/43 staining) and myelinating oligodendrocytes (BCAS1 staining) in lesion D. I,J) chronic inactive lesions showed demyelination and lack of microglia/macrophages (MBP-CR3/43 staining, I-1,2 & J-1,2) and appeared hyperintense in QSM (I-3, J-3). K,L) chronic active lesions showed demyelination and rim of microglia/macrophages in edges (MBP-CR3/43 staining, I-1,2 & J-1,2) and showed hyperintense paramagnetic rims in QSM (I-3, J-3).

Like reference symbols in the various drawings indicate like elements.

DETAILED DESCRIPTION

Figure 1A:
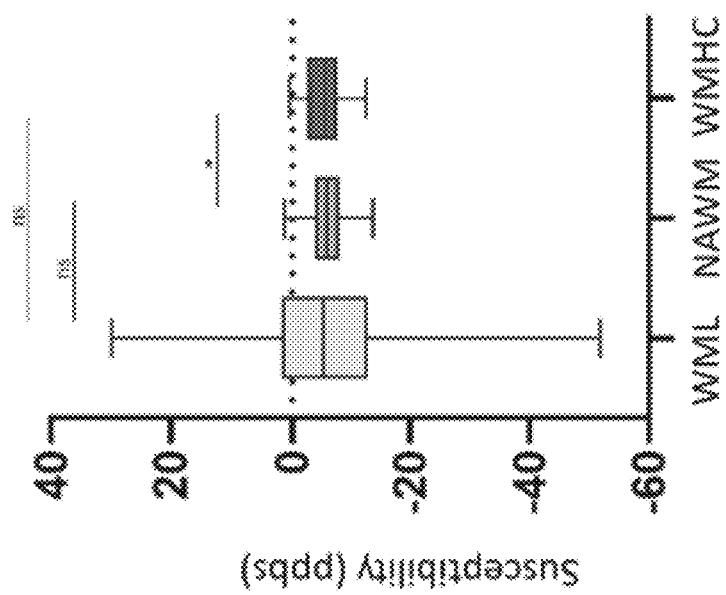
FIGS. 1A-1B show susceptibility values in white matter lesion (WML), normal appearing white matter (NAWM), and white matter in healthy control (WMHC).

Implementations of systems and methods for collecting and processing magnetic resonance imaging (MM) signals of a subject, and reconstructing maps of biophysical properties intrinsic to the subject (e.g., magnetic susceptibility) are described below. The noninvasiveness and rich tissue contrasts of MRI are explored and utilized to characterize pathological, physiological and therapeutical changes in brain tissues for monitoring neurological patients. Multiple MRI tissue contrasts including T2 contrast, T2* or R2*=/1/T2* contrasts, and magnetic susceptibility contrasts are employed in tissue characterization. In some of the disclosed implementations, quantitative susceptibility mapping (QSM) and related postprocessing of gradient echo data are developed and applied for characterizing remyelination of multiple sclerosis (MS) lesions.

In some implementations for monitoring remyelination in MS patients using MM, the method comprises obtaining a T2 weighted magnetic resonance image with a hyperintense contrast for a MS lesion; obtaining complex gradient echo magnetic resonance images, wherein the complex image comprises magnitude and phase information regarding the MS lesion; determining an image of quantitative susceptibility map of the MS lesion based on the obtained complex magnetic resonance data; determining characteristic features of the MS lesion on the quantitative susceptibility map, wherein identifying the characteristic features comprises registering the T2 weighted image with the quantitative susceptibility map, identifying a T2 region of a lesion where the lesion appears hyperintense on the T2 weighted image, determining a susceptibility distribution in the T2 region of the lesion, determining a susceptibility distribution in a region of tissue surrounding in the T2 region of the lesion, partitioning the T2 region of the lesion into three groups, hyperintense subregions, isointense subregions and hypointense subregions, by comparing the susceptibility distribution in the T2 region of the lesion with the susceptibility distribution of the region of tissue surrounding the T2 region of the lesion; and determining remyelination in the MS lesion according to a characteristic feature of a hypointense subregion and/or an isointense subregion of the lesion.

In some implementations, to characterize features of a MS lesion, the lesion region is segmented on T2 weighted image, which is referred as the T2 region of the lesion. The magnetic susceptibility distribution from QSM over the T2 region is partitioned into three groups as hyperintense subregion, isointense subregion, and hypointense subregion, by comparing the lesion with its surrounding normal appearing tissue on QSM. The partition can be performed based on susceptibility value distribution and/or spatial connectivity distribution characteristics. The partition may be performed using a clustering method based on one or more such distributions.

In some implementations, comparing the susceptibility distribution in the T2 region of the lesion with the susceptibility distribution of the region of tissue surrounding the T2 region of the lesion comprises measuring susceptibility values on the quantitative susceptibility map.

In some implementations, to reconstruct maps of a subject's magnetic susceptibility, the computation process of finding the susceptibility distribution that optimally fit available gradient echo MRI (GRE) data and tissue structure prior information is made accurate by fitting data at each echo time without compromising the precision in modeling data noise. For gradient echo (GRE) magnetic resonance imaging data obtained by a magnetic resonance scanner, the GRE data at each echo time is complex, its magnitude and phase information or real and imaginary information regarding the object is well characterized to have Gaussian noise in the domain of complex signal. This GRE data should be generally interpreted as multiple echoes with both magnitude and phase evolving with echo times. Gradient echo, spin echo and hybrid echo and other type of pulse sequences can be used to acquire these multiple echoes.

In some implementations, reconstructing maps of a subject's magnetic susceptibility comprises using the phase information and additional information. The additional information may comprise known tissue structural information, such as sparsity in certain mathematical representations, including various norms of edge operations, total variation, and wavelets. The additional information may be learned from training dataset using deep neural network.

In some implementation, determining the quantitative susceptibility map comprises identifying a region of interest in the tissue that has an approximately uniform susceptibility and enforcing the known uniform susceptibility value in the region of interest in the tissue. The approximate uniform susceptibility region may be identified by a low R2* value derived from the GRE data. R2* values are used as the characteristic feature for identifying regions at various susceptibility contrasts. R2* values can be readily obtained from multiecho complex data. The region of interest at a given susceptibility contrast can be determined by similar R2* properties of contiguous voxels, and the penalty there depends on a representative R2* value in the region of interest. Enforcing the known uniform susceptibility value may be realized using a regularization of specific cost function or using a deep neural network and training that effectively provide an implicit regularization.

In some implementation, determining the quantitative susceptibility map comprises using a data fidelity term associated with a likelihood function associated with a Gaussian noise. The Gaussian likelihood function may be imposed rigorously in the complex gradient echo data domain, or approximately in various data domain, such as the phase or field data domain.

In some implementations, to characterize a MS lesion, the susceptibility distribution of the lesion is evaluated and compared with the susceptibility distribution of surrounding normal appearing tissue. For example, the region of tissue surrounding in the T2 region of the lesion may comprise a layer of normal appearing white matter and/or gray matter surrounding the lesion. Determining characteristic features comprises using a susceptibility value measured on the quantitative susceptibility map.

In some implementations, determining characteristic features comprises using multiple parameters determined from magnetic resonance imaging. In some implementations, determining a characteristic feature comprises calculating a R2* map from the gradient echo magnetic resonance images and determining a myelin quantity from the R2* map and quantitative susceptibility map according to a calibrated curve.

In an example embodiment, a method for generating one or more images of an object comprises: obtaining complex magnetic resonance data collected by a magnetic resonance scanner, wherein the data is complex and comprises magnitude and phase information regarding the object; estimating a magnetic susceptibility distribution of the object based on the obtained complex magnetic resonance data, wherein estimating the magnetic susceptibility distribution of the subject comprises determining a cost function, the cost function including a data fidelity term involving modeling a magnetic susceptibility effect on complex magnetic resonance data, a regularization term involving a first region with a low feature of susceptibility contrasts, and a second region with a feature of susceptibility contrasts different from the feature of susceptibility contrasts of the first region; minimizing the cost function; determining a magnetic susceptibility distribution based on the act of minimizing the cost function; and presenting, on a display device, one or more images of the object generated based on the determined magnetic susceptibility distribution.

1. Quantitative Susceptibility Mapping Identifies Remyelinated, Chronic Active and Chronic Inactive Multiple Sclerosis Lesions In this section, a magnetic resonance imaging technology for monitoring remyelination in multiple sclerosis is discussed.

1.1 Introduction

Quantitative susceptibility mapping (QSM) quantifies the spatial distribution of magnetic susceptibility within biological tissues and provides measures that are sensitive to both iron accumulation and myelin integrity in the brain. QSM has been used to identify white matter (WM) lesions with a rim of iron-laden microglia/macrophages in multiple sclerosis (MS) patients (paramagnetic rim lesions-PRL), which histopathologically correspond to chronic active and smoldering lesions. Besides, QSM has been applied to assess the longitudinal evolution of acute MS lesions over time. Nevertheless, to date, QSM has not been exploited for classifying the heterogeneity of MS lesion types that are reported in neuropathological studies.

Indeed, MS patients exhibit a variety of MS lesion types, due to heterogeneity in initial targets of injury, activity status and extent of repair, i.e., remyelination and axonal regeneration. Among MS lesions, there is a variable extent of myelin and axon damage and iron content. Myelin content in MS lesions is highly variable. Following subsequent waves of de- and re-myelination, MS lesions might present the final phenotype of demyelinated, partly remyelinated and shadow plaques (fully remyelinated lesions). Lesions location (i.e., periventricular vs juxtacortical regions), age (i.e., acute vs chronic lesions), cellular composites (i.e., presence of oligodendrocytes and microglia/microphages), and the clinical disease subtype (i.e., RRMS vs PMS) also significantly contribute to the heterogeneity of remyelination activity.

Axonal damage in MS lesions is largely heterogeneous as well. Acute axonal transection occurs more commonly in active demyelinating lesions, whereas inactive MS lesions show delayed degeneration of long-term demyelinated axons, owing to excitotoxity mechanisms and innate inflammation. In chronic active and smoldering lesions, extensive axonal damage occurs both at the center and at the lesion border.

Iron content is likewise extremely diverse across the different lesion types. Many—but not all—active MS lesions harbor iron-laden macrophages. Shadow plaques contain higher amount of iron compared to smoldering or inactive MS lesions. Furthermore, chronic active lesions are also characterized by an iron-laden rim of microglia/macrophages at their edge.

Currently, MS lesion types can be differentiated neuropathologically, but the distinction of MS lesion types in vivo (i.e., remyelinated vs chronic active/smoldering vs chronic inactive) remains challenging. In this disclosure, an integrated multi-contrast approach, including QSM, Myelin Water Imaging and diffusion MM, is applied in order to disentangle MS lesions heterogeneity in vivo in MS patients.

Myelin water imaging (MWI) and biophysical models applied to multi-shell diffusion MIll offer more specific surrogate measures of myelin and axon content than other advanced Mill techniques. MWI quantifies the water between myelin layers by distinguishing multiple water components in T2 relaxometry data and supports with measures (e.g., myelin water fraction, MWF), which have been validated postmortem.

Multi-compartment microscopic diffusion imaging (MCMDI) is a technique that provides estimates of intraneurite compartment as neurite density index (NDI) and extra-neurite compartments in the brain, which has also been applied to MS patients. The advantage of MCMDI over DTI is that MCMDI does not assume a Gaussian distribution of diffusion processes and, hence, models non-Gaussian diffusion in biological tissue providing more specific measures of tissue microstructure.

In this disclosure, MS lesions were classified according to their visual appearance on QSM maps, and myelin and axonal damage were studied among QSM lesion types by using MWF and NDI. Further, a combined histopathology-QSM evaluation was performed in two post-mortem MS brains to assess the histopathological correlates of the in vivo QSM classification of MS lesions.

1.2 Materials and Methods

Participants: 115 MS patients (76 RRMS and 39 PMS) were enrolled and 76 healthy controls (HC) and demographic and clinical characteristics are reported in Table 1. Inclusion criteria were: (i) MS diagnosis according to McDonald criteria from 2017 and diagnosis of active RRMS or inactive progressive MS (PMS) according to standard practice; (ii) absence of any concomitant psychiatric or neurological disease (excluding headache); (iii) absence of contraindication to MRI. All patients (n=115) enrolled in this study also underwent a conventional MRI (cMRI) during the 3 months before the study. All Gd enhancing lesions in cMRI were excluded from the following analyses. The study was approved by the local ethic review committee of and all participants following written consent entered the study. Eleven patients were excluded because of motion artifacts in QSM images.

TABLE 1

| | Multiple sclerosis subjects | Healthy control subjects |
| --- | --- | --- |
| Sex, n (male/female) | 115 (48/67) | 76 (32/45) |
| Age (years), mean ± SD | 46 ± 14 | 35 ± 13 |
| EDSS score, median (range) | 3.14 (0-8) | — |

TABLE 1-continued

| | Multiple sclerosis subjects | Healthy control subjects |
| --- | --- | --- |
| Disease course (RR/PMS) | 76/39 | — |
| Disease-modifying therapy (n) | Untreated (13) | |
| | Interferon-beta (1) | |
| | Glatiramer acetate (1) | |
| | Dimethyl fumarate (15) | |
| | Fingolimod (9) | |
| | Natalizumab (4) | |
| | Rituximab (13) | |
| | Ocrelizumab (55) | |
| | Siponimod (2) | |
| | Teriflunomide (2) | |

MR acquisition: MM was performed on a 3T whole-body MR system (Prisma, Siemens Healthcare, Erlangen, Germany) using a 64-channel phased-array head and neck coil. The MRI protocols included: (i) 3D FLAIR (TR/TE/TI=5000/386/1800 ms) with 1 mm3 isotropic spatial resolution; (ii) Fast Acquisition with Spiral Trajectory and adiabatic T2prep (FAST-T2) (spiral TR/TE=7.5/0.5 ms, six T2prep times=0 (T2prep turned off), 7.5, 17.5, 67.5, 147.5, 307.5 ms, voxel size=1.25×1.25×5 mm$^3$, scan time=4.5 min, as described in (Nguyen et al., 2016); (iii) multi-shell diffusion (TR/TE/$\delta$/$\Delta$/resolution=4.5 s/75 ms/19 ms/36 ms/1.8 mm$^3$ isotropic with b-values 0/700/1000/2000/3000 s/mm$^2$ with 12/6/20/45/66 measurements, respectively, per shell and a diffusion acquisition with 12 measurements of b-value 0 s/mm$^2$ with reversed phase encoding as well as (iv) 3D segmented EPI with submillimeter isotropic resolution (TR/TE/resolution=64 ms/35 ms/0.67×0.67×0.67 mm$^3$).

Diffusion images were denoised and corrected for motion and eddy-currents. Multi-Compartment Microscopic Diffusion Imaging (MCDMI) diffusion model was used, which is a state-of-the-art model that integrates the spherical mean technique to handle orientation dispersion and fiber crossing populations, allowing more accurate estimations in whole-brain voxels. From this model, the neurite density index (NDI), which corresponds putatively to the intra-axonal volume fraction, was estimated.

Quantitative susceptibility mapping (QSM) is a field-to-source inversion method to map the local susceptibility sources in the tissue from the shift in the magnetic field created by these sources which can be measured from gradient echo data. In this disclosure, QSM were reconstructed from 3D EPI data by unwrapping phase, removing the background field through use of the projection onto dipole fields algorithm, and using the morphology-enabled dipole inversion algorithm to compute the susceptibility from the local field.

Post-mortem imaging and histopathology: Postmortem MS brains from two secondary-progressive MS patients (disease duration respectively 8 and 24 years, respectively) were imaged on a 3T whole-body MR system (Prisma$^{Fit}$, Siemens Healthcare, Erlangen, Germany) using a 20-channel head and neck coil and a dome-shaped brain-container filled with perfluoropolyether. The brains were fixed directly in 4% neutral buffered formaldehyde solution (formalin) within 24 hours from the time of death and for about 4-6 months before the time of MM. Post-mortem QSM images were reconstructed using three dimensional-echo planar imaging (3D-EPI) (330 µm isotropic, TR=65 ms, TE=35 ms, ETL=13, bandwidth 394 Hz/Pixel). An individualized cutting box for each brain was then designed and 3D-printed. Additional manual registration between the digitized brain slab surfaces and the corresponding MM slices were performed to further refine the match between histopathological and MRI images. Region of interest (ROI) including MS lesions were identified on 3D-EPI images and manually segmented using ITK-SNAP 3.6.0.

Histopathologically, WM lesions and remyelinated areas were identified and then categorized by means of anti-myelin basic protein (MBP, for myelin), Anti-CR3/43 (for MHCII-expressing macrophages/activated microglia) and anti-breast carcinoma-amplified sequence 1 (BCAS1) IHC (for myelin and actively myelinating oligodendrocytes). Shadow plaques were characterized on Luxol fast blue (LFB)-stained slides. Digital processing of whole slide images was performed using an open microscopy OMERO server (version 5.6.3).

Lesion identification and segmentation: Segmentation of WM lesions (WMLs) was performed using a cascade of two convolutional neural networks adapted to use FLAIR and MP2RAGE MRI contrasts as inputs. Manual correction of segmented WM lesion masks on FLAIR was performed by two experienced readers by consensus (RR and CG).

QSM lesion types were classified as follows: First, a map of MS lesions was obtained through automatic detection and segmentation as detailed above; then (ii) the FLAIR lesion map was registered to the QSM map using a boundary-based registration from the FMRIB Software Library (FSL) so that MS lesions could then be identified in the QSM map; afterwards, (iii) MS lesions were classified according to their appearance on QSM at intensity range −200+200 parts per billions (ppbs): i) iso-intense (i.e., lesions that showed no intensity difference in QSM maps compared to the surrounding tissue) ii) paramagnetic rim lesions-PRL (lesions with hyperintense rim in QSM maps) iii) lesions with hypointense rim relative to the lesion center iv) hyperintense lesions v) hypointense lesions (FIGS. 2A-2J).

To find dominantly myelin-damaged and dominantly axon-damaged WM lesions (i.e. lesions with a larger % change in MWF and NDI, respectively), the relative proportion of myelin and axonal damage in WMLs relative to the respective values in the contralateral hemisphere (% MWF and % NDI reduction) was calculated as follows: (mean MWF or NDI in the mirror region of interest (ROI) in the contralateral hemisphere—mean MWF or NDI in lesion)×100/the value in the mirror ROI in contralateral hemisphere. For this purpose, all lesions exhibiting contralateral NA mirror areas were selected in the lesion masks. In total, 85 lesions out of 2,852 WMLs were selected and the mirror ROIs were then manually contoured.

WM and cortex segmentation: Using FreeSurfer (v.6.0, surfer.nmr.mgh.harvard.edu), the brain was segmented into whole WM, cortex, deep grey matter structures, and ventricles. NAWM mask was produced by subtracting WM lesion mask from WM mask. Output of Freesurfer was further used to identify a 2-voxel layer of NAWM and NAGM surrounding the lesions on FLAIR; hereinafter denoted as peri-plaque WM (PPWM). The relative susceptibility for individual WMLs was calculated as follows: Susceptibility lesion-Susceptibility PPWM.

WM masks were automatically divided into periventricular (PV, i.e., area within 3 mm from ventricular wall), juxtacortical (JC, i.e., area in 3 mm from the interface between WM and cortex), and deep white matter (DW, i.e., area between PV and JC).

All values, including intra-lesional, PP tissue and homogeneous non-lesional NA tissue, were automatically extracted both in lesion-wise and average patient-wise manners.

Clustering of Iso-/Hypo-intense lesions vs PRLs—To confirm that the qualitative appearance of QSM lesion types represents lesions with different MWF, NDI and susceptibility, a Gaussian Mixture Model (GMM) was applied to the lesion groups exhibiting the highest and lowest MWF/NDI/susceptibility mean content and assumed the presence of two clusters. Finally, the percentages of QSM lesion types (i.e. Iso-/Hypointense lesions vs PRLs) falling into two distinct clusters that were identified were calculated. When PRLs and hypointense/isointense lesions were considered, the GMM identified two clusters: 80.23% of PRLs clustered in the area with low MWF and NDI values (FIGS. 2G-2I), while 72.55% of hypointense and 68.15% of isointense lesions clustered in the area with high MWF and NDI values (FIGS. 2G-2I).

Statistical analysis was performed using GraphPad Prism version 8.0.0 for Windows, GraphPad Software, San Diego, Calif. USA. A Kolmogorov-Smirnov's test was used to assess the normality of data. Paired t-test, non-parametric Mann-Whitney test, and Kruskal-Wallis test with Dunn's test for multiple comparisons correction, were used for the paired two-group analysis, the unpaired two-group analysis, and the more-than-three group analysis, respectively.

1.3 Results

Average susceptibility alterations in MS white matter lesions: The patient-wise average of magnetic susceptibility in white matter lesions (WMLs) in MS patients (n=104) was not different from the susceptibility in normal appearing white matter (NAWM) and from the one in white matter in healthy controls (WM-HC) (P>0.05). However, the average susceptibility was lower in NAWM than in WM-HC (P=0.014). (FIG. 1A).

Figure 1B:
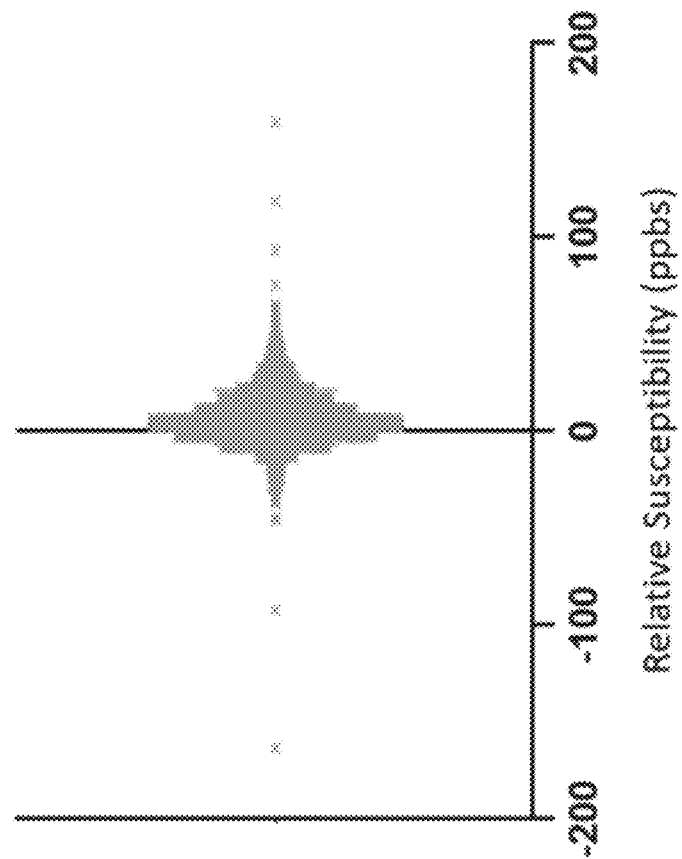

Relative Susceptibility in WMLs: lesion-wise analysis: In 2852 WMLs, the lesion-wise analysis showed that the susceptibility in MS WM lesions relative to 2-voxel-sized peri-plaque WM (PPWM) exhibited values ranging from −163.7 ppbs to +159.00 ppbs. In 814/2852 WML (28.54%), a negative relative susceptibility and in 2038/2852 71.46% a positive relative susceptibility was measure, as shown in FIG. 1B.

Classification of MS lesions on QSM maps: Out of 2852 WM lesions, 1621 showed peculiar characteristics and were classified in (i) isointense lesions (n=476 29.4%), paramagnetic rim lesions-PRL lesions (n=210, 13%), hypointense rim (hypo-rim) lesions (n=20, 1.23%), hyperintense lesions (n=846, 52.2%) and hypointense lesions (n=69, 4.26%), as shown in FIGS. 2A-2J and Table 2, below. A total of 1231 lesions were not included in this classification mainly due to big traversing vessels, artifacts and non-uniform signal intensity in the lesional area.

Figures 2A, 2B:
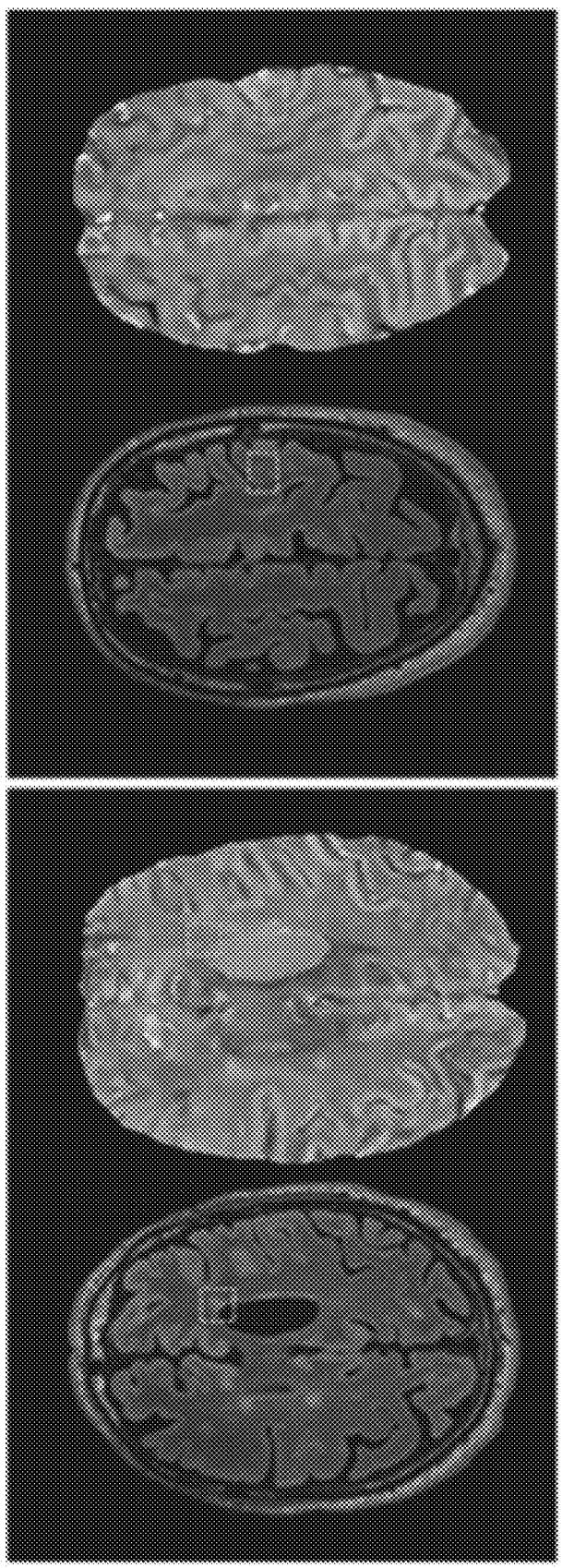
FIGS. 2A-2J show QSM lesion types: A) Isointense, B) Hypointense, C) Hyperintense, D) Hypo rim, E) Paramagnetic rim lesion (PRL), F) Comparison of susceptibility values among QSM lesion types. G, H) Myelin water fraction and neurite density index comparison among QSM lesion types. I, J) Lesion-wise analysis of myelin water fraction (MWF) and neurite density index (NDI) comparison across QSM lesion types.
Figure 2D:
Figure 2C:
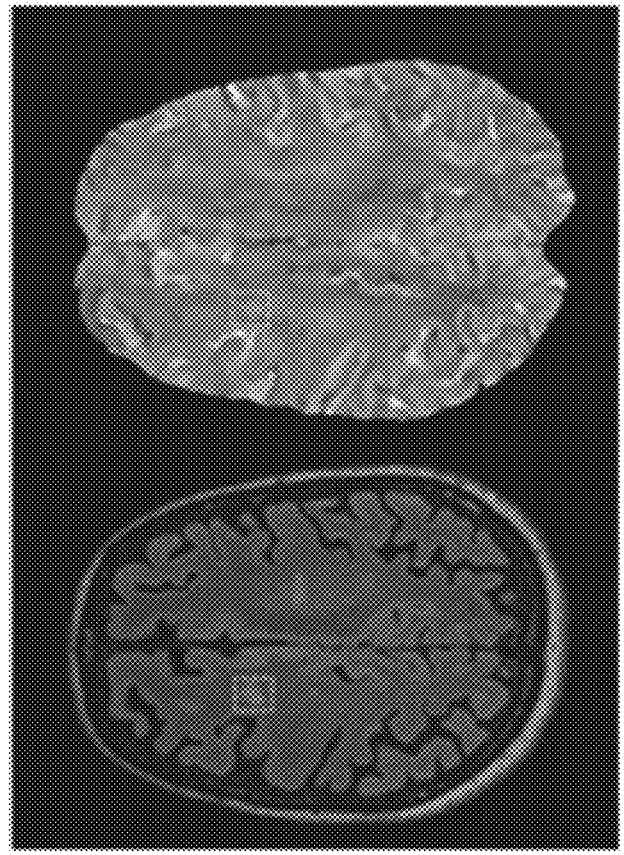
Figure 2E:
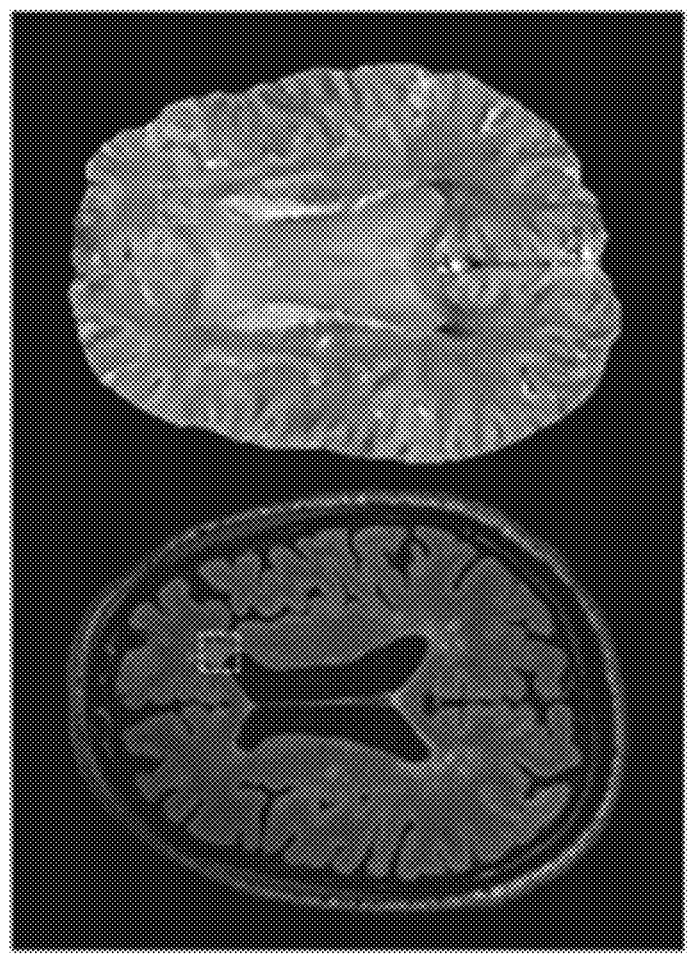
Figure 2F:
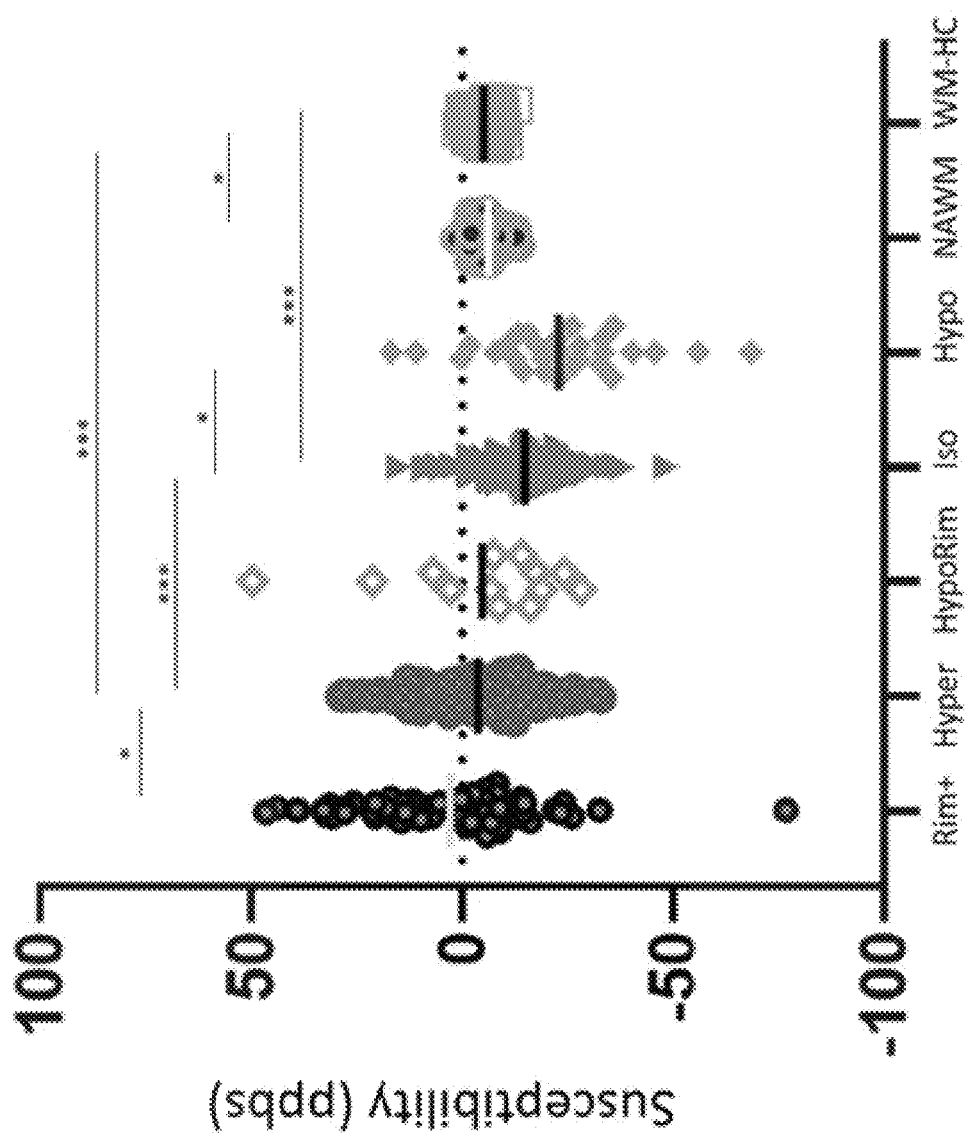
Figure 2G:
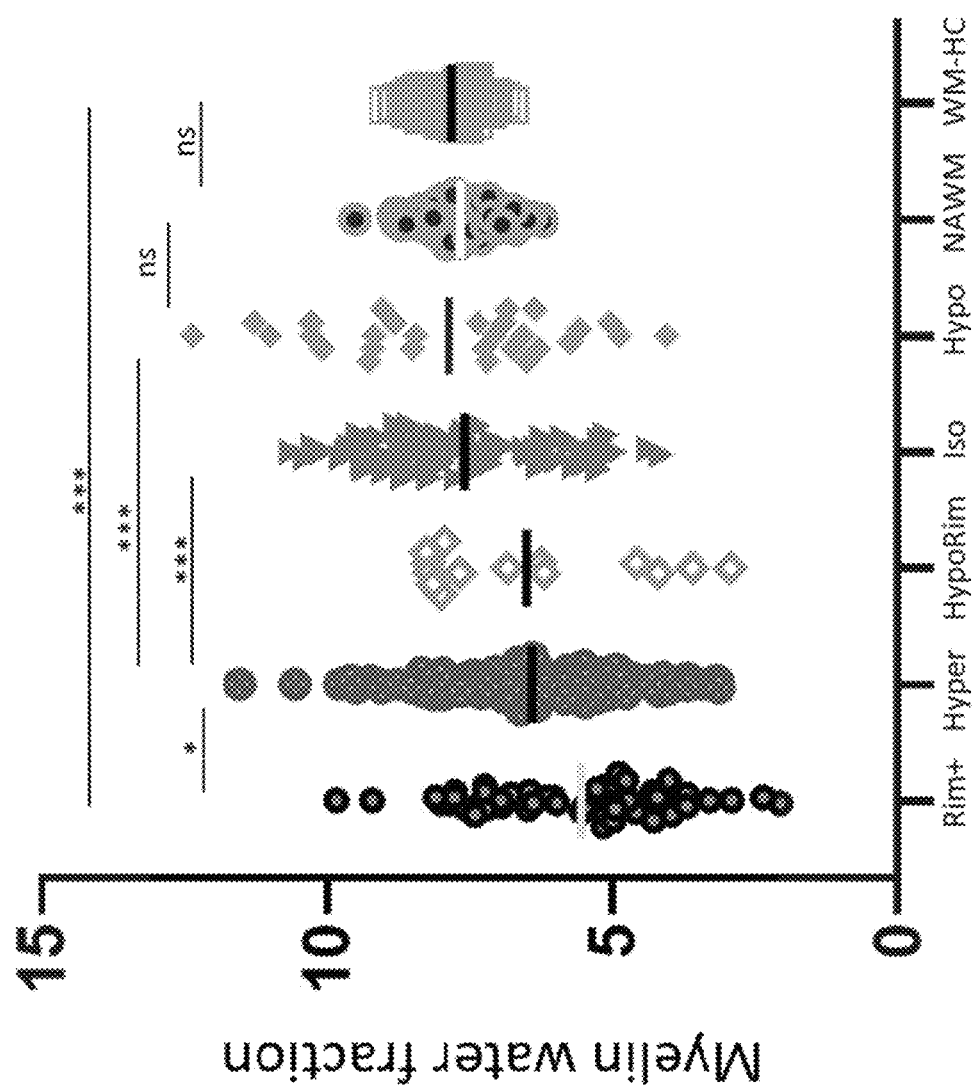
Figure 2H:
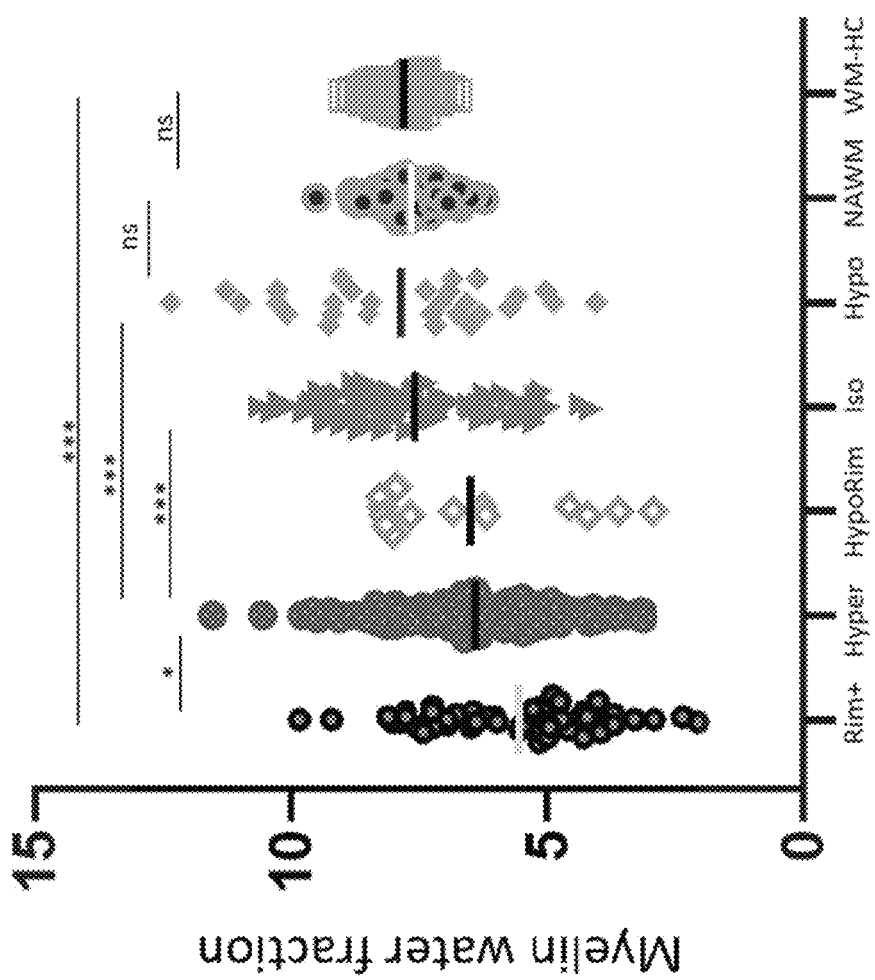
Figure 2I:
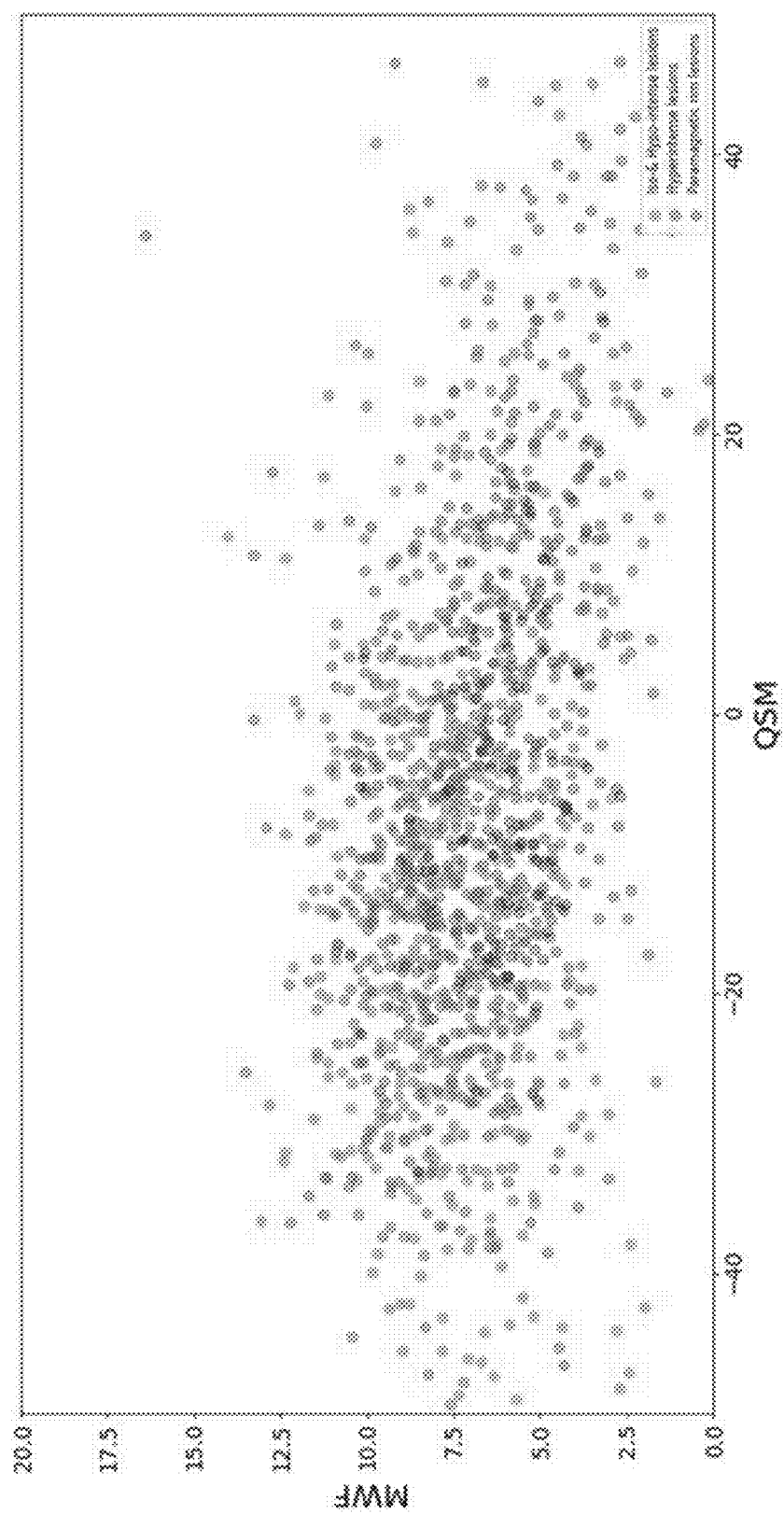

Hypointense lesions on QSM showed lower magnetic susceptibility than isointense lesions (P<0.0001), isointense lesion showed lower magnetic susceptibility than hyperintense lesions (P<0.0001) and hyperintense lesions showed lower magnetic susceptibility than PRL lesions (P=0.014), as shown in FIG. 2F.

TABLE 2

| QSM lesion types | RRMS quantity (%) | PMS quantity (%) |
|---|---|---|
| Isointense | 330 (28.2%) | 146 (32.44%) |
| Hypointense | 37 (3.2%) | 32 (7.11%) |
| PRL | 150 (12.8%) | 60 (13.33%) |
| Hyperintense | 637 (54.39%) | 209 (46.44%) |
| HypoRim | 17 (1.5%) | 3 (0.7%) |

Susceptibility comparison between lesions with dominant axon or myelin damage: 85 WMLs exhibiting contralateral mirror areas without focal lesions were selected and categorized into lesions with dominant axon or myelin damage according to the relative MWF and NDI changes, the relative MWF was assessed, and NDI changes were categorized into lesions with dominant axon or myelin damage. There was no difference in average susceptibility between lesions with predominant damage to axon or myelin (4.064±17.67, 7.759±21.80; P>0.05). In addition, no difference was found when the mean NDI was compared between lesions with positive and negative relative susceptibility (0.3644±0.1131, 0.3496±0.1109; P>0.05).

MWF and NDI in QSM lesion types: Isointense lesions exhibited higher NDI (P<0.05) and MWF (P<0.0001) compared to visible lesions. Isointense lesions exhibited also lower NDI compared to NAWM and WM-HC (P<0.0001). On the other hand, MWF in isointense lesions was not different from NAWM and WM-HC (P>0.05). Nevertheless, isointense lesions exhibited higher MWF and NDI than hyperintense and PRL lesions (P<0.0001). Last, there was no difference in MWF and NDI between Isointense and Hypo-rim lesions (both P>0.05), as shown in FIGS. 2G and 2H.

Hypointense lesions exhibited lower NDI (P<0.0001) compared to NAWM and WM-HC. There was also a trend in the average MWF that was lower in hypointense lesions compared to NAWM and WM-HC (P>0.05). In comparison to other QSM lesion types, hypointense lesions showed higher MWF and NDI than hyperintense and PRL lesions (both P<0.0001). MWF was lower in hypointense lesions than in hypo-rim lesions (P<0.05), however NDI was not different (P>0.05), as shown in FIGS. 2G and 2H.

Hyperintense lesions exhibited lower MWF and NDI compared to NAWM and WM-HC (P<0.0001) and higher MWF (P=0.0029) and NDI compared to PRL (P<0.001), as shown in FIGS. 2G and 2H.

PRL lesions showed lower MWF and NDI compared to WM-HC, NAWM and compared to all other QSM lesion types (P<0.001), as shown in FIGS. 2G and 2H.

Figure 2J:
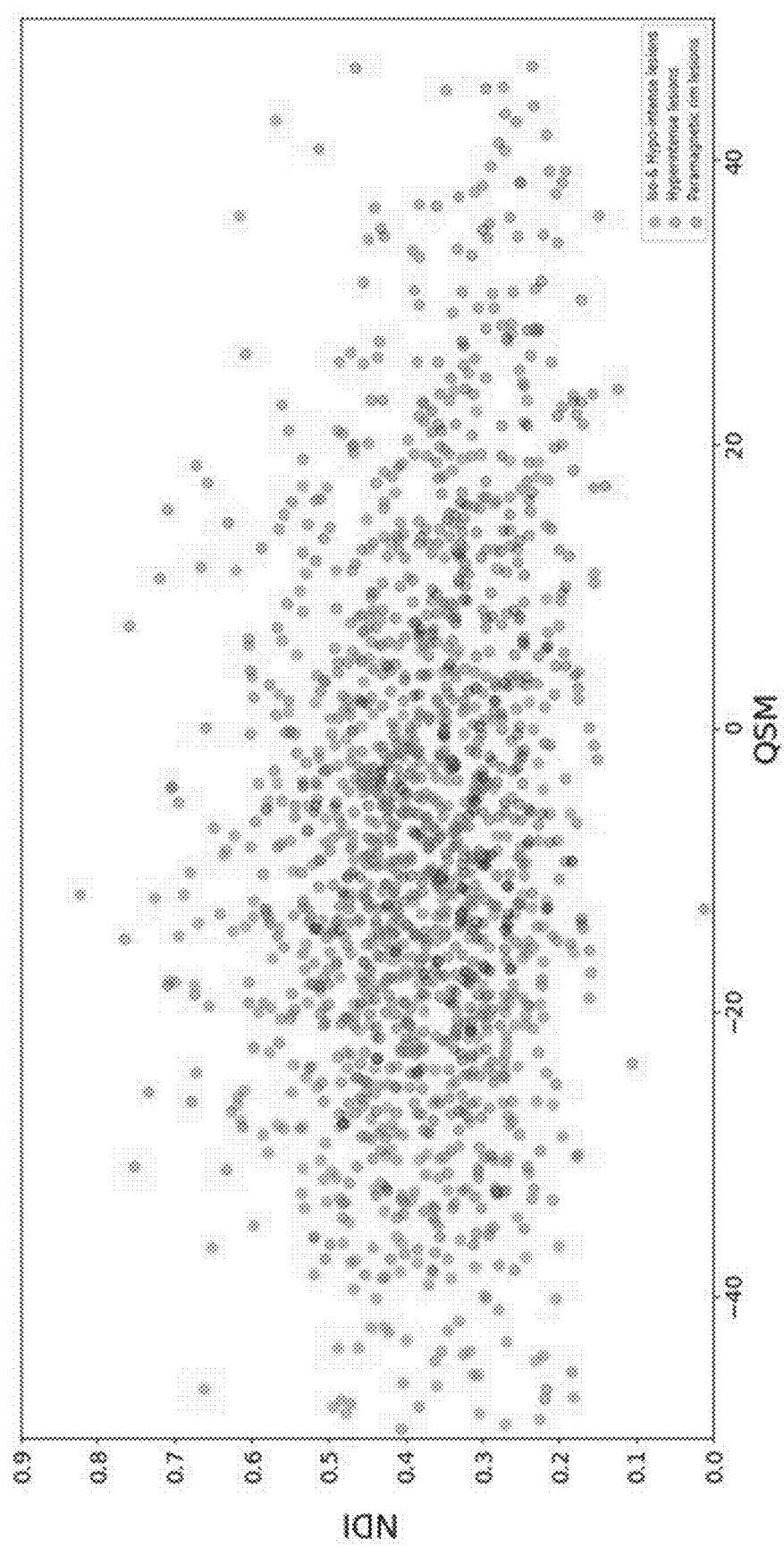

Lesion-wise analysis confirmed the results reported for the patient-wise analysis, as shown in FIGS. 2I-2J.

Figure 4:
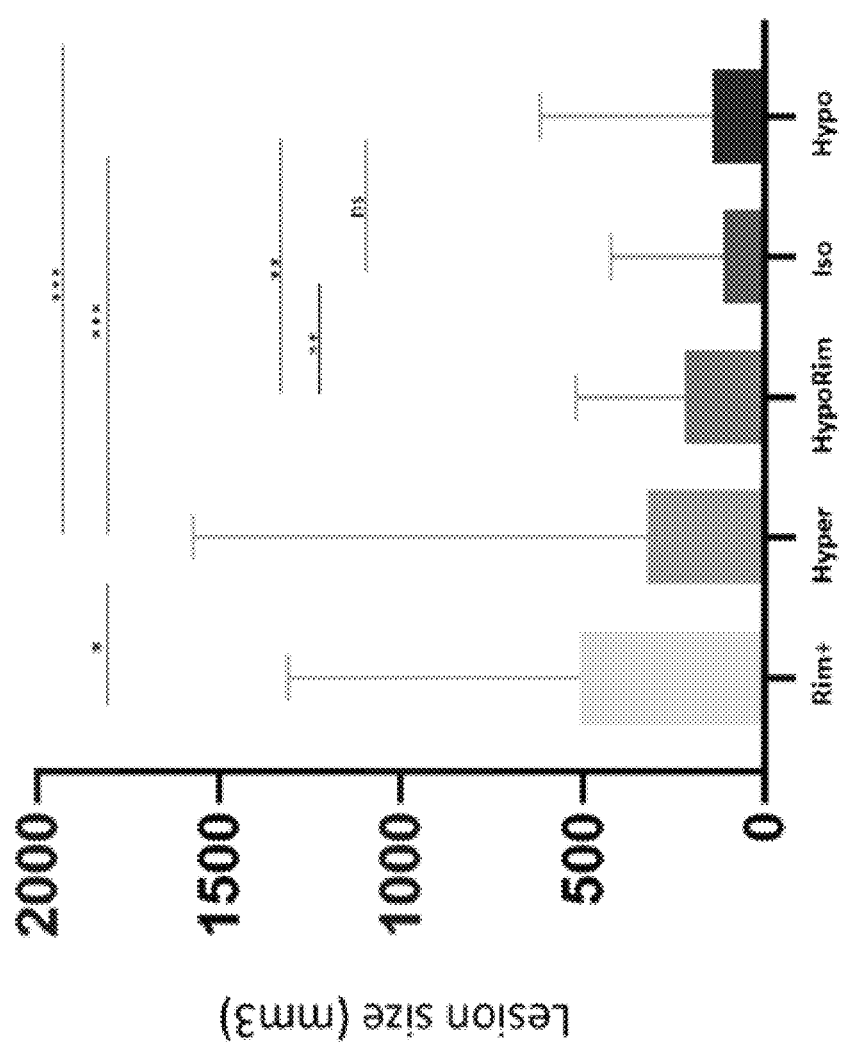
FIG. 4 shows comparison of lesion size across QSM lesion types.

Comparison of lesion size across QSM lesion types: Hypointense lesions and isointense lesions were smaller than hyperintense lesions (P=0.0003, P<0.0001), which in turn were smaller than PRL lesions (P<0.0001), as shown in FIG. 4.

There was no difference in the frequency of QSM lesion types between RRMS and PMS patients (all P>0.05). PRL lesions were predominantly located in PV regions (P<0.05) and hypointense lesions mainly in JC areas (P<0.001). Isointense and hyperintense lesions were evenly distributed across PV, JC and DW regions.

Combined histopathology-QSM study of two post-mortem MS brain: To confirm the QSM findings in vivo, the QSM appearance of histopathologically-classified MS lesions, which were identified in two post-mortem MS brains, was studied.

Remyelinated areas and lesions (4/6 lesions) with scarce presence of microglia and BCAS cells were hypointense/isointense in QSM images in comparison to the surrounding NAWM; when iron-rich microglia/macrophages were observed in the lesions (2/6 lesions), the areas corresponding to remyelinated lesion tissue in QSM were however hyperintense when compared to the surrounding NAWM, as shown in FIGS. 3A-3H.

Figure 3A:
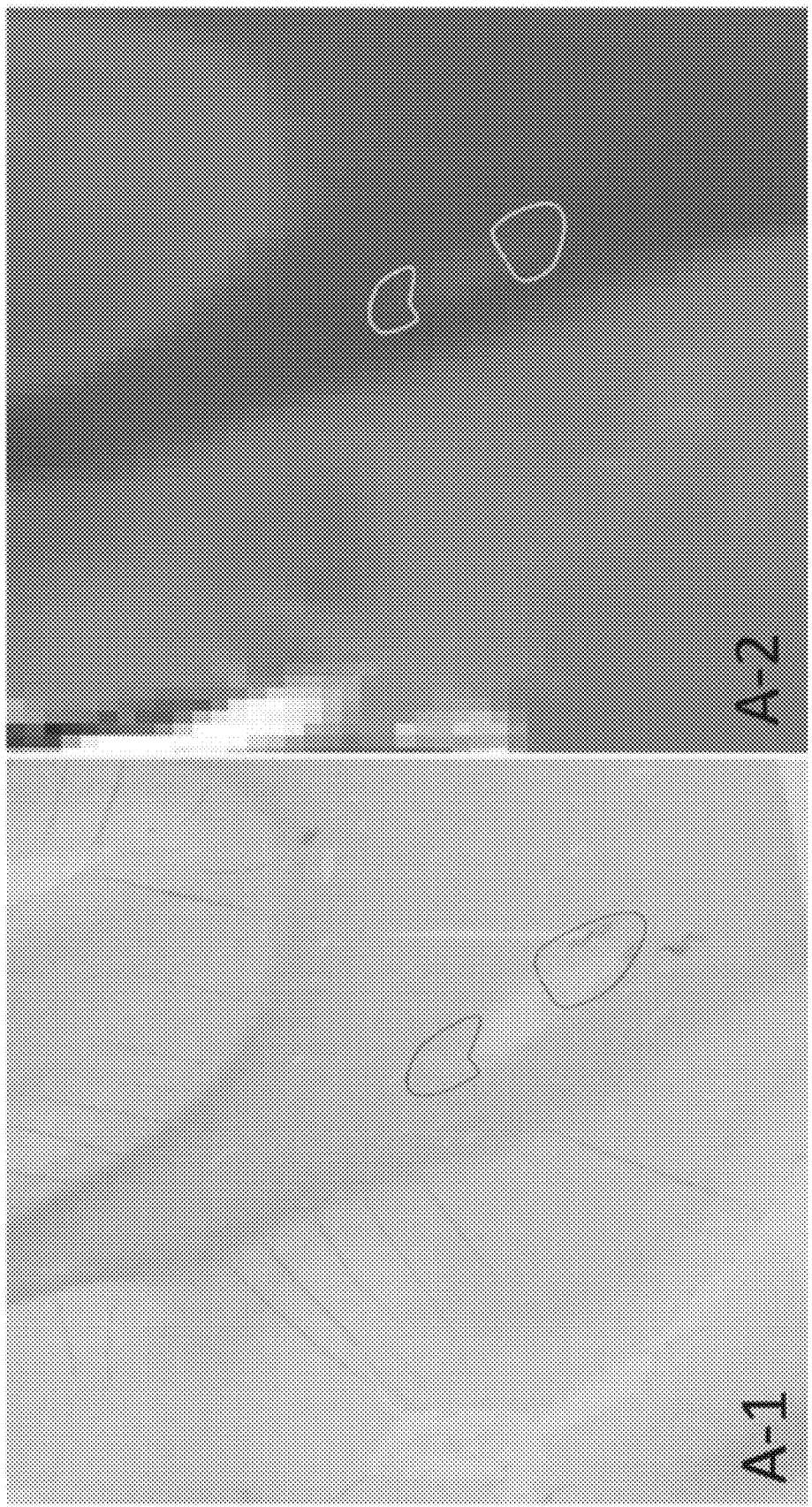
Figure 3B:
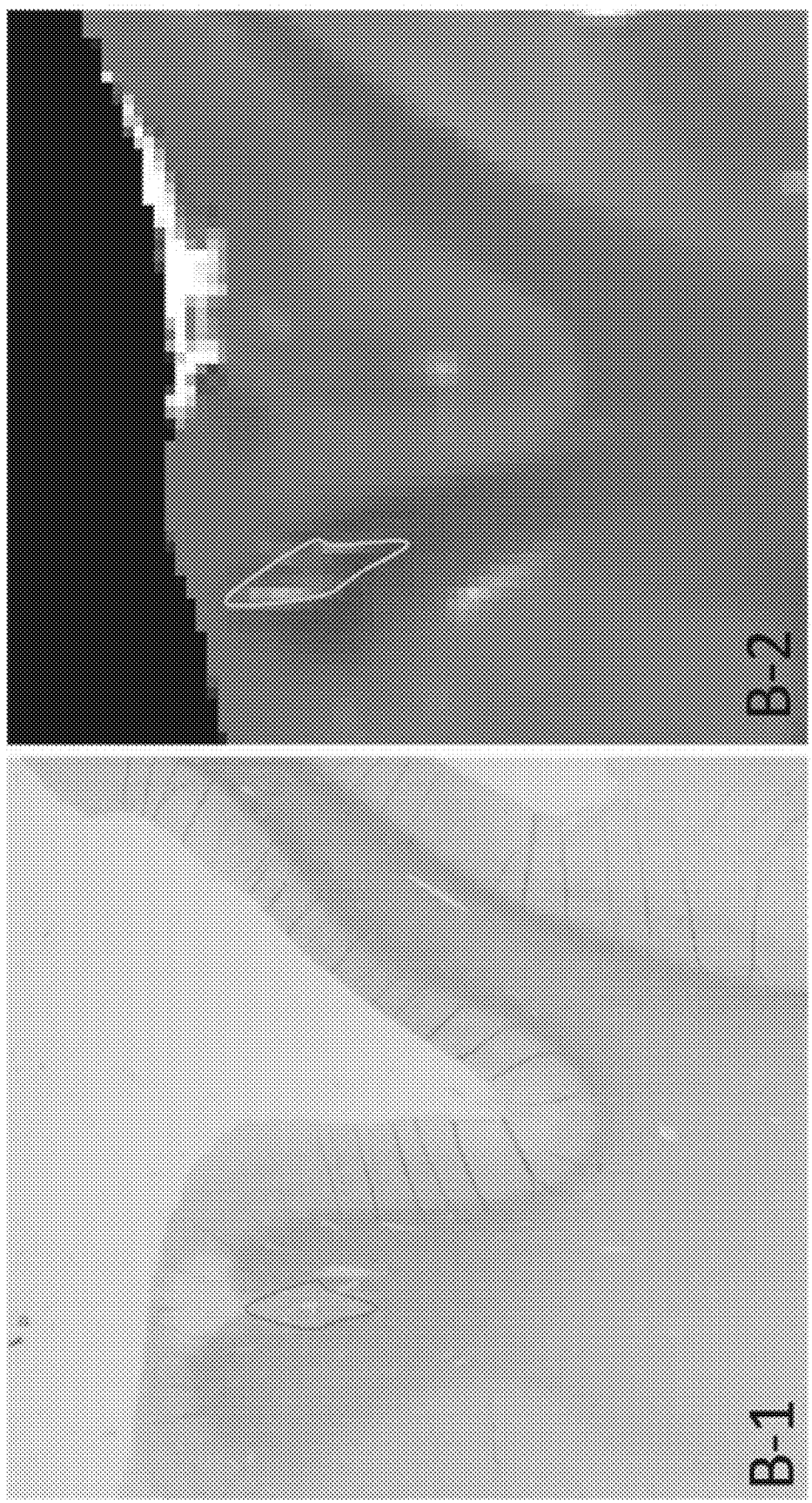
Figure 3C:
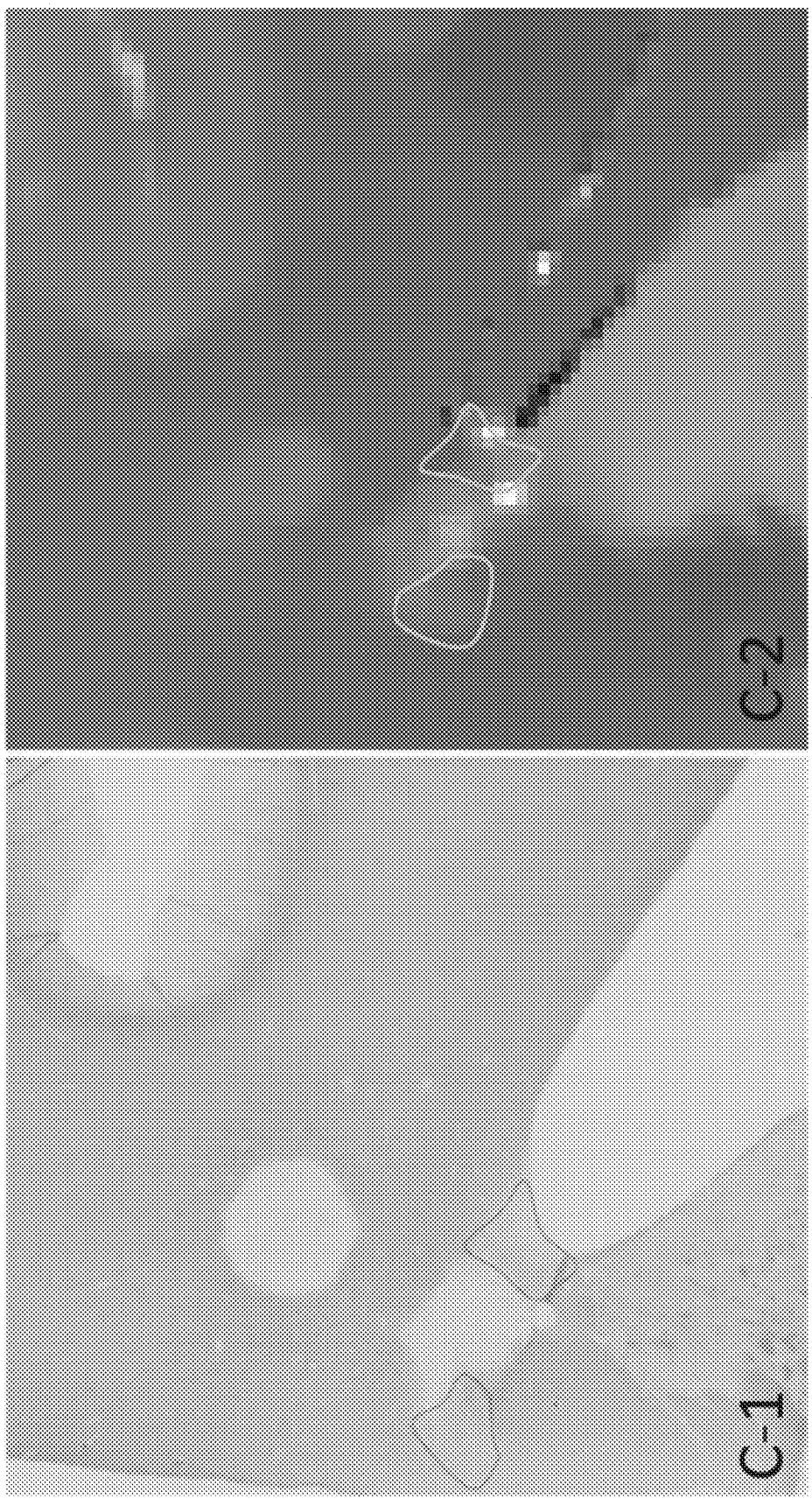
Figure 3D:
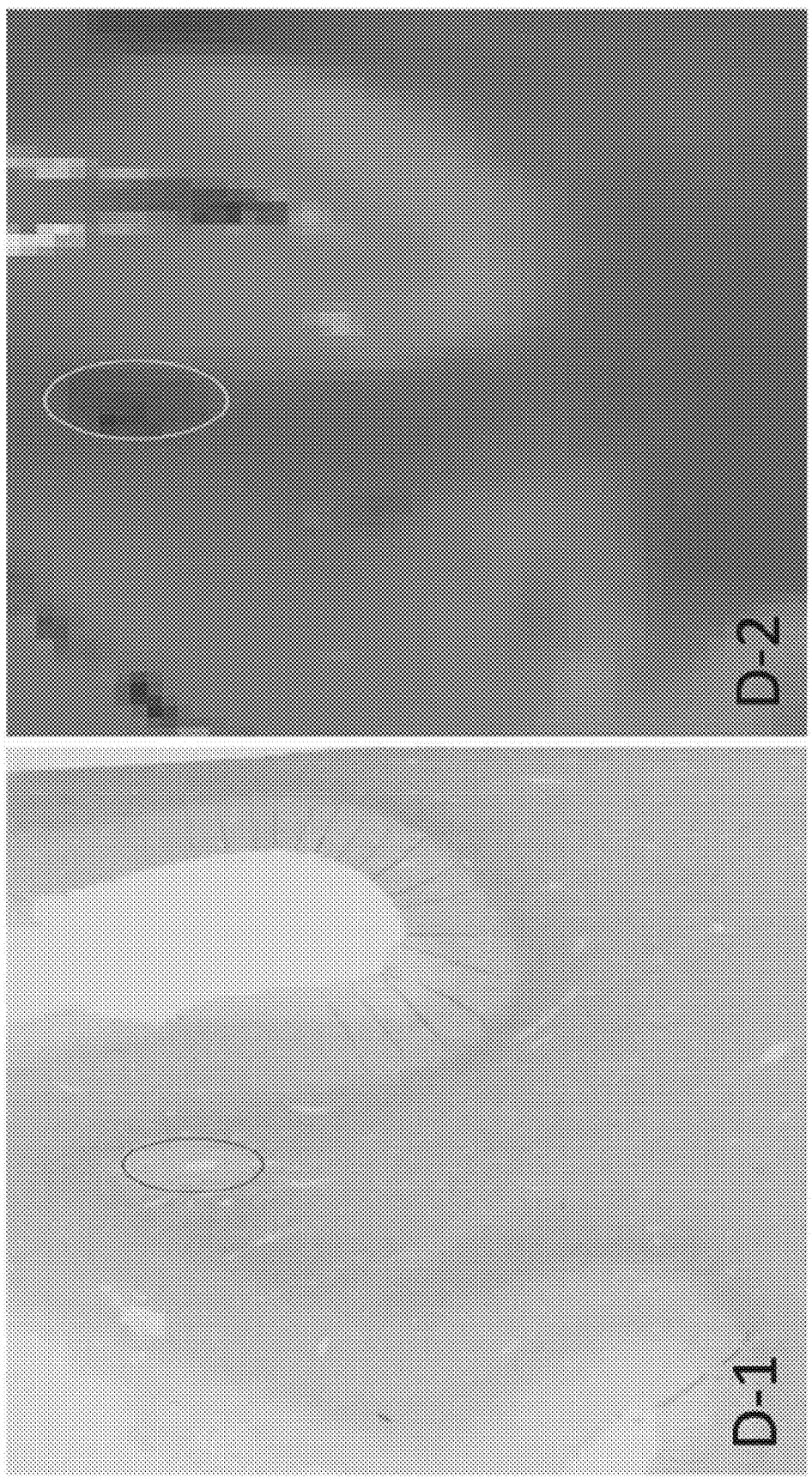
Figure 3E:
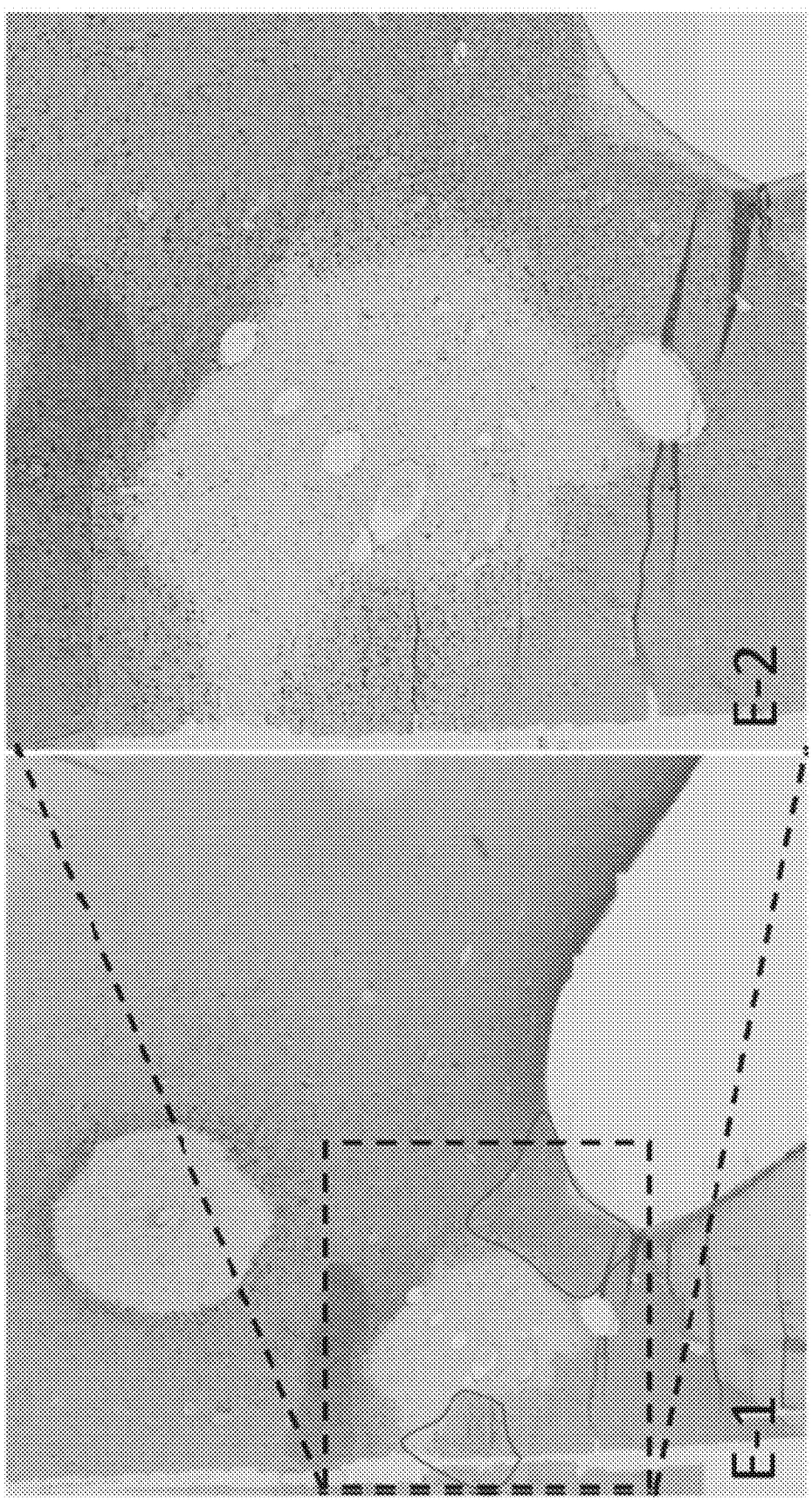
Figure 3F:
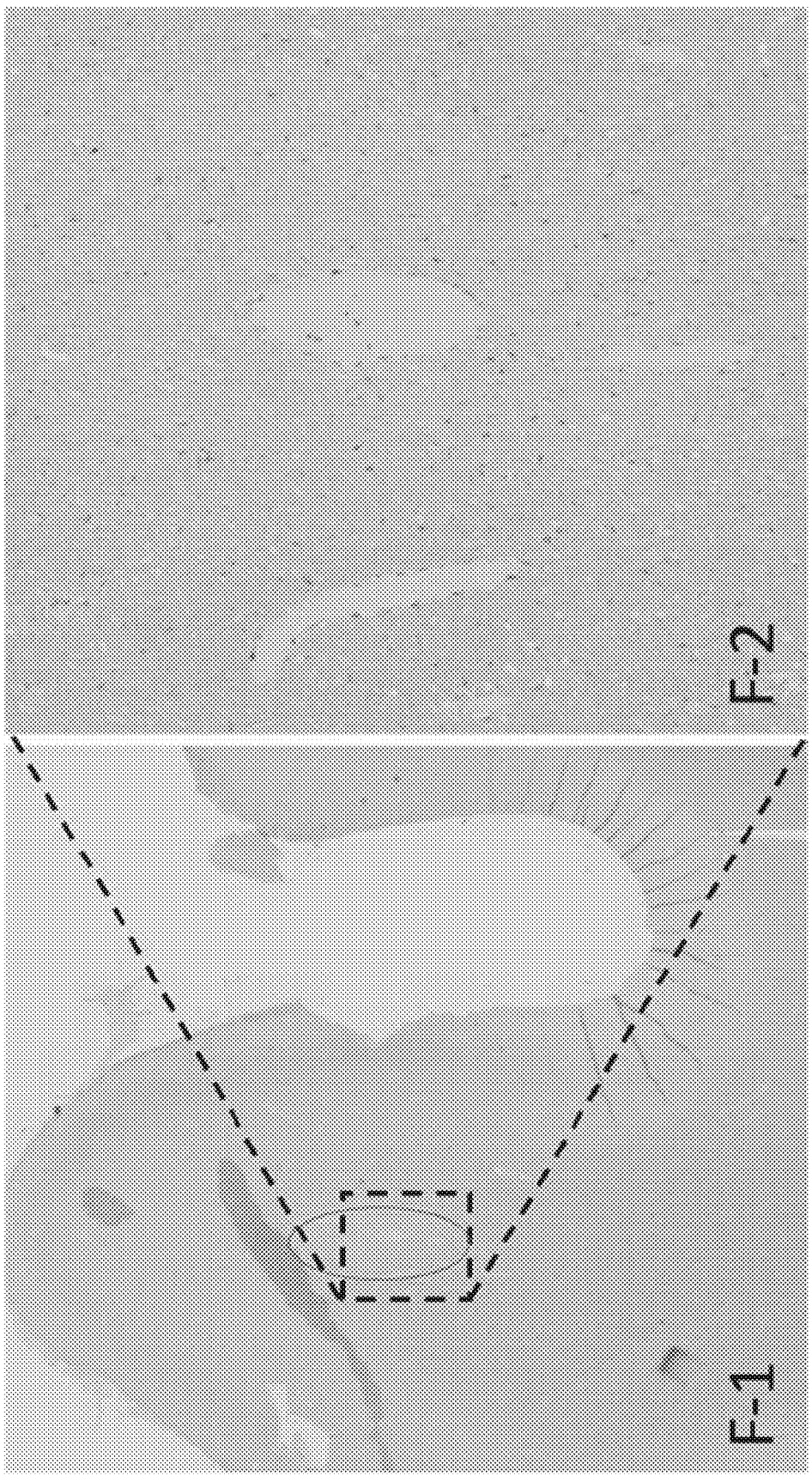
Figure 3G:
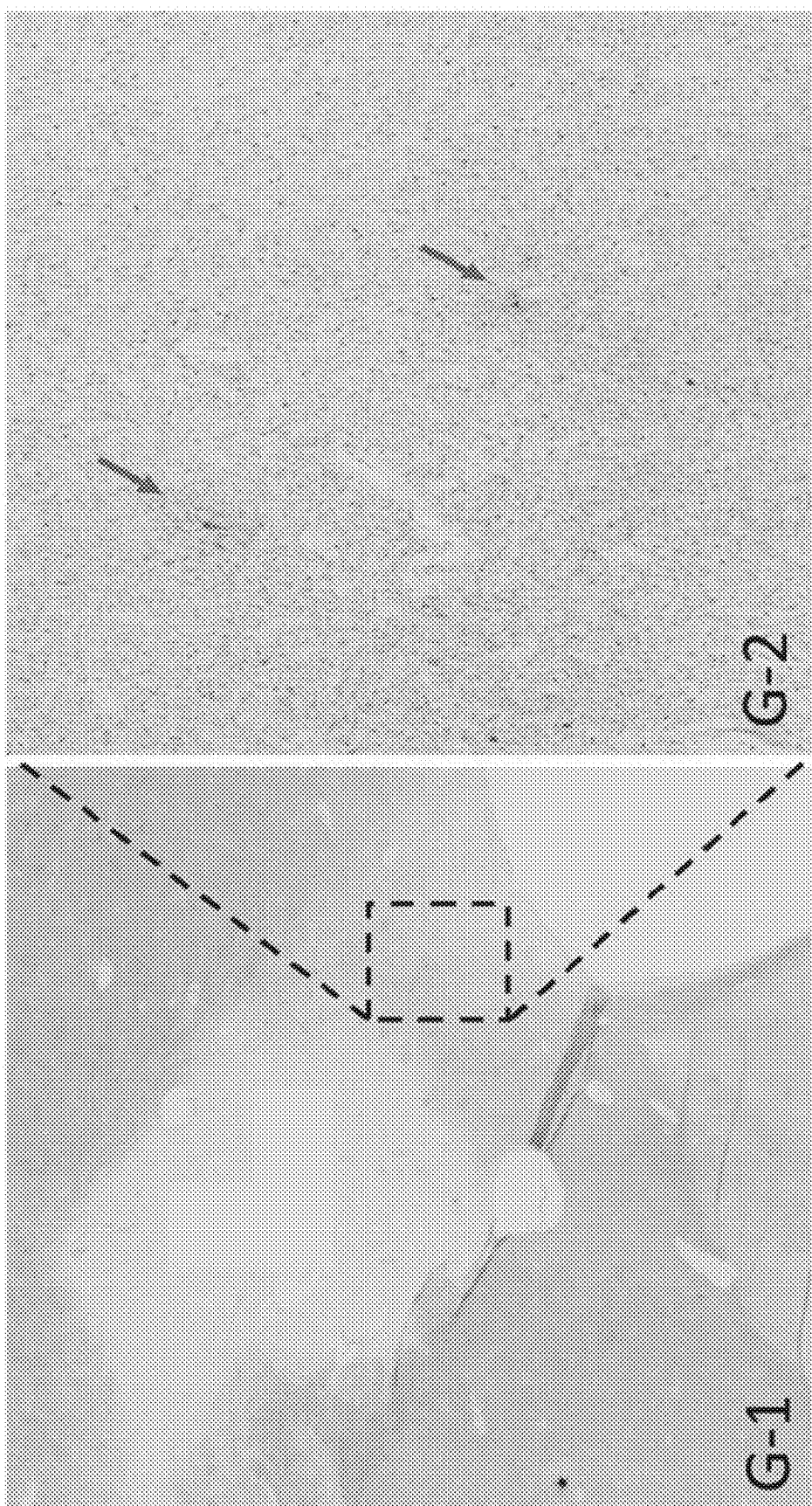
Figure 3I:
Figure 3J:
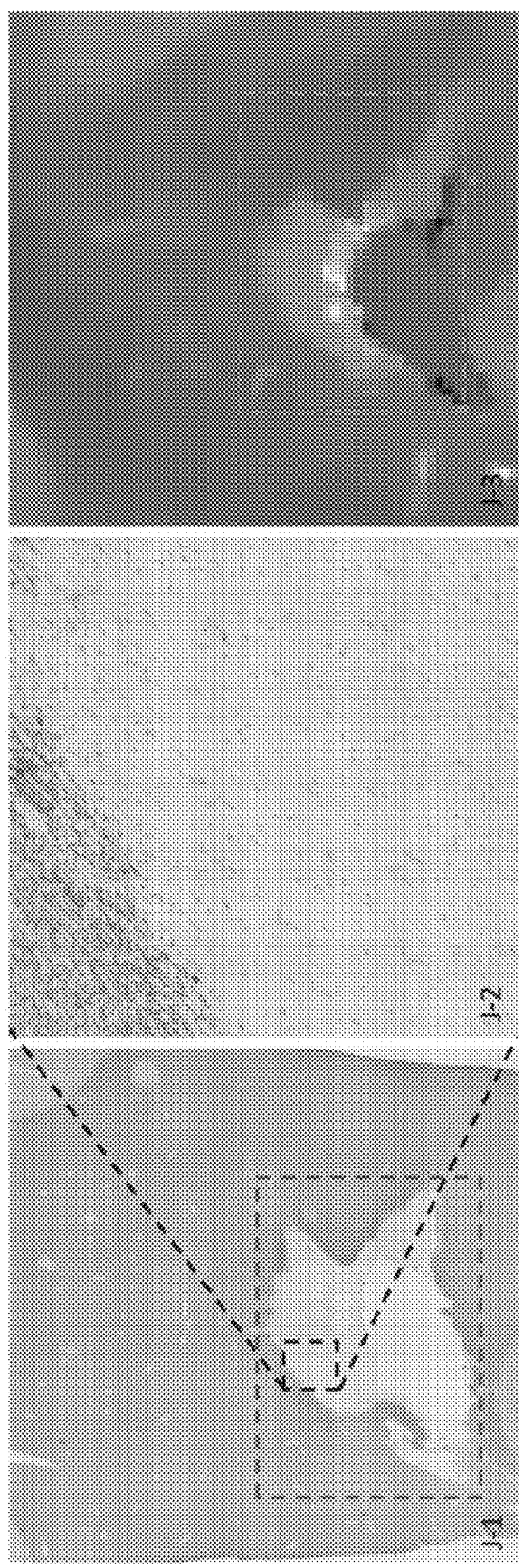
Figure 3K:
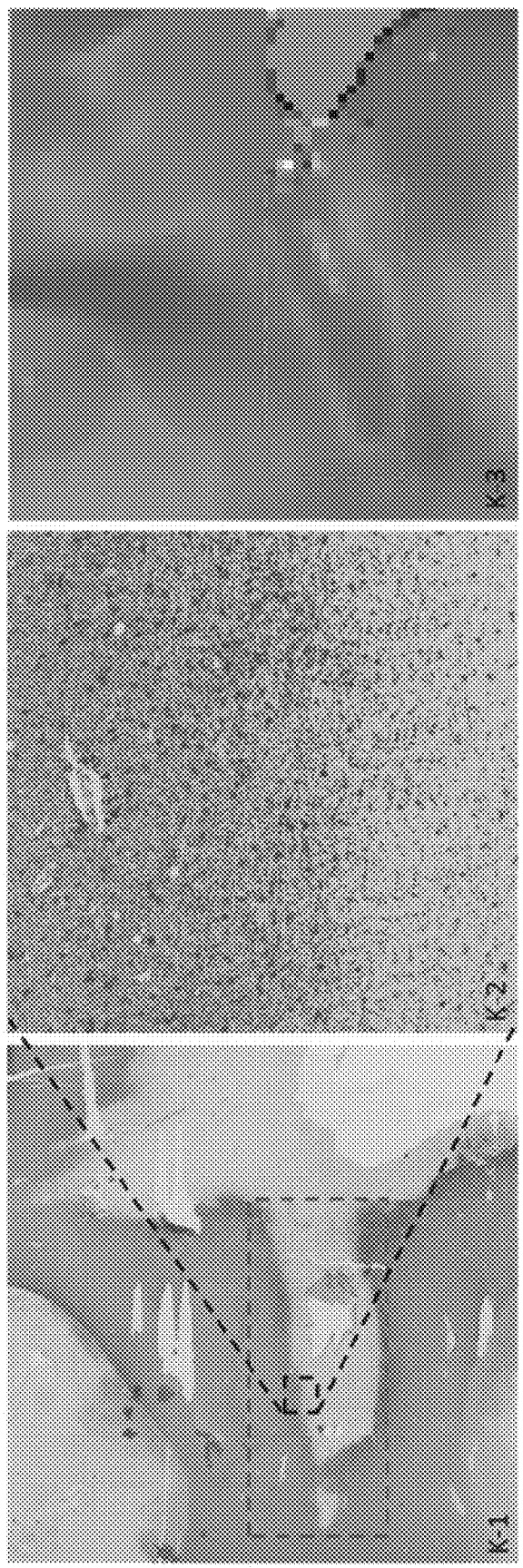
Figure 3L:

Both the chronic inactive and the chronic active lesions (5/5 lesions) appeared hyperintense at QSM, as shown in FIGS. 3I-J), and chronic active lesions (4/4 lesions) showed hyperintense paramagnetic rim, as shown in FIGS. 3K and 3L.

1.4 Further Description

QSM computes the susceptibility map from a susceptibility field, typically with the field first estimated by fitting a signal model to the acquired GRE images. In this disclosure, five MS lesions types in QSM maps have been identified and their relative axon and myelin content in vivo in MS patients are quantified. These 5 QSM lesion types exhibited changes in susceptibility and in myelin/axon characteristics that exhibit imaging features compatible with some specific histopathological lesion subtypes, namely (i) chronic active/smoldering, (ii) chronic inactive and (iii) remyelinated lesions. An additional combined postmortem QSM-histopathology-study confirmed this association.

Previous studies related some characteristics of MS lesions in QSM maps to lesion-age and to the presence of acute and chronic focal inflammation. Specifically, acute lesions were shown to have a lower susceptibility relative to surrounding NAWM, whereas chronic active/smoldering lesions were hyperintense and exhibited a characteristic rim of high-susceptibility at the edge, which was shown to represent iron accumulated in active macrophages and microglia.

In this disclosure, QSM lesion types that had been previously described (hyperintense, PRL and isointense) have been identified and some others that are being reported for the first time (hypo-rim, hypointense). Furthermore, new evidence has been provided that QSM lesion types substantially differ for myelin and axon content, as measured using as MWF and NDI.

In accordance with previous neuropathological works and imaging studies, the majority of WM lesions in the cohort of MS patients showed a positive relative susceptibility in QSM maps, which was probably driven by iron accumulation in microglia, macrophages and oligodendrocytes 30 as well as loss of myelin integrity.

Hypointense lesions showed the lowest susceptibility and highest myelin and axon content compared to other QSM lesion types, suggesting that they may represent remyelinated plaques. In fact, the average MWF in these lesions was at the level of the one measured in NAWM and in the WM of healthy controls.

Similarly, isointense lesions showed higher myelin and axon content compared to the other lesion types (PRL, hypo-rim and hyperintense) and a comparable one to hypointense lesions. Yet, isointense lesions exhibited a higher susceptibility than the hypointense lesions, probably due to ongoing iron accumulation (eg. in remyelinating oligodendrocytes or microglia/macrophages as shown in FIGS. 3E&3F). It was previously shown that acute lesions mostly appear isointense on QSM: however, in this disclosure, Gd+ lesions that were evident in a cMRI performed within 3 months from the study MRI were excluded. Hence, the presence of active lesions in the cohort is relatively improbable.

Supporting the hypothesis that hypointense and isointense lesions are remyelinated is also the observation that those lesions exhibited significantly less axonal damage than other lesions, hereby reflecting the findings of previous neuropathological studies showing that axonal density is higher and acute axonal transection is lower in remyelinated areas than in demyelinated areas. Furthermore, both in vivo and postmortem that iso- and hypointense QSM lesion types correspond to lesions where full remyelination has occurred: this is in line with the fact that fully remyelinated lesions or lesion areas are less rich in activated microglia/macrophages and oligodendrocytes than areas with ongoing remyelination, rendering their susceptibility essentially influenced by the myelin content. To date, numerous treatments are available that target the acute inflammatory component of the MS disease. However, drugs fostering remyelination and repair are lacking. The identification of imaging biomarkers of axonal and myelin repair is fundamental to drive the development of targeted neuroprotective and reparative drugs. This disclosure provides new evidence that QSM maps may be used to identify fully remyelinated lesions in vivo in MS patients, opening then a perspective to evaluate—at least in part—the repair capacity of existing and novel MS therapies.

Magnetic susceptibility across QSM lesion subtypes was inversely related to MWF and NDI (as shown in FIGS. 2F-2J). In fact, lesions with the highest susceptibility (i.e., PRL and hyperintense lesions) also showed the lowest MWF and NDI, suggesting extensive demyelination, axonal loss and iron deposition: this latter may be also deemed responsible for oligodendrocytes death and pro-inflammatory microglia-activation in these lesions.

PRL lesions have been previously described as hyperintense QSM lesions that are characterized by a rim of activated and iron-rich microglia leading to smoldering demyelination and axonal loss. Also in the post-mortem study, those plaques corresponded to the histopathological subtypes of chronic active and smoldering lesions.

On the other hand, hyperintense QSM lesions exhibited highest susceptibility probably due to pronounced iron deposition and tissue loss, as it is typical of hypocellular and gliotic chronic inactive lesions. Indeed, in the post-mortem study, chronic inactive lesions appeared hyperintense in QSM, hereby confirming the interpretation of the multiparametric analysis in vivo in MS patients. Further, consistent with previous QSM studies performed in vivo and works focusing on chronic inactive lesions postmortem, QSM hyperintense lesions were the most frequent QSM lesion type in the cohort of MS patients.

Interestingly, PRL lesions were mainly located around the ventricles, which is a region characterized by plaques with destructive nature, as a result of the release of demyelinating antibodies and myelin-reactive immune cells and cytokines from ventricles. In contrast, hypointense lesions were mainly located in the juxta-cortical area, which is a region with potentially high remyelinating capacity thanks to more numerous and efficacious oligodendrocyte precursor cells.

MS lesions rarely appeared with a hypointense rim around a relatively hyperintense center in QSM. The lower susceptibility of rim compared with the center could signify a destructive damage leading to tissue loss, probably in late stages of chronic active/smoldering lesions. This lesion type is relatively rare.

Surprisingly, the distribution of QSM lesion types did not differ between RRMS and PMS patients, showing that differences in MS lesion types are not associated with different clinical phenotypes.

It is noted that, although excessive iron accumulation may put demyelinated axons under devastating oxidative stresses, the data showed that axonal damage did not differ between lesions with positive relative susceptibility and lesions with negative relative susceptibility. Further, susceptibility was not different between lesions with predominant-axonal and predominant-myelin damage. The contribution of both iron and myelin content to QSM susceptibility as well as the dual role of iron in oxidative damage and in fostering remyelination and repair may partly account for these findings.

In accordance with the disclosure, QSM maps permit classification of MS lesions with various extent of damage and repair to myelin and axon. QSM correlates of fully remyelinated lesions have also been identified histopathologically. The temporal evolution and dynamics of the different QSM lesion classes, as well as their sensitivity to treatment, may also be assessed.

2. Determine Characteristic Features of Multiple Sclerosis Lesions on QSM

In this section, a method for determining characteristic features of multiple sclerosis (MS) lesions on QSM is described.

MS lesions are defined on conventional T2 weighted imaging, with or without fluid attenuated inversion recovery. Specifically, a T2 region of a lesion where the lesion appears hyperintense on the T2 weighted image is identified. This lesion T2 region is represented by a binary mask Mt2. A region surrounding Mt2 is also identified to contain normal appearing white matter (NAWM) and normal appearing gray matter (NAGM), and this region of tissue surrounding Mt2 is represented by a binary mask Mst. All MRI images are co-registered, and the masks Mt2 and Mst can be applied to all images.

The susceptibility distributions in Mt2 and Mst are determined from QSM. The susceptibility distribution of NAWM in Mst is denoted as wMst, and the susceptibility distribution of NAGM in Mst is denoted as gMst. The susceptibility distribution in Mt2 is denoted as sMt2. A clustering analysis is performed to partition Mt2 into a hyperintense subregion denoted as M+ with a susceptibility distribution sM+, an isointense subregion denoted as M0 with a susceptibility distribution sM0, and a hypointense subregion denoted as M− with a susceptibility distribution sM−.

In some implementations, the clustering analysis is executed using a distribution-based clustering analysis, including simple rectangular distribution, which is thresholding. In an exemplary implementation, wMst, sM+, sM0 and sM− are modeled as rectangular distributions in the susceptibility value space or bins in the susceptibility histogram domain. Then sM+ corresponds to the bin with susceptibility values above the bin defined by wMst, sM0 corresponds to the bin defined by wMst, and sM− corresponds to the bin below the bin defined by wMst. The width of sM+ and sM− can be adjusted to accommodate all points above and below the wMst bin.

In another exemplary implementation, wMst, sM+, sM0 and sM− are modeled as Gaussian distributions in the susceptibility value space. Then the mean of sM+ is higher than the mean of wMst, the mean and standard deviation of sM0 are the same as that of wMst, and the mean of sM− is lower than the mean of wMst. The standard deviations of sM+ and sM0 can be adjusted to provide optimal accommodation of all points using the expectation-maximization (EM) algorithm. The EM iterative algorithm can be applied here comprises the following steps: 1. Initialize estimates for parameters for means and standard deviations for sM+ and sM−. 2. (Expectation) Compute the likelihood weights for each voxel susceptibility value in Mst. 3. (Maximization). Update the estimates for the parameters using the maximum likelihood estimator formula. 4. Repeat steps 2 and 3 until reaching a convergency criterion is satisfied.

Then sM0 and sM− are used to monitor remyelination in multiple sclerosis. Remyelination may occur in response to therapy. The number of voxels in M0 and M−, the mean of sM−, and the product of the number of voxel in M− and the mean of sM− representing a magnetic moment, as well as other measures generated from sM0 and sM−, can be used to characterize the degree of remyelination.

In some implementations, the gradient echo (GRE) data can be further processed for myelin quantification. Iron contributes to GRE signal R2* decay and increases susceptibility value; myelin contributes to GRE signal R2* decay but decreases susceptibility value. The dependances of R2* and magnetic susceptibility on the concentrations of iron and myelin can be determined according to calibrated curves. Then myelin and iron concentrations can be determined according to the calibrated curves.

The myelin concentration is then used in the clustering analysis, such as the distribution-based clustering analysis. For simplicity to keep the same sign and notations as the above QSM, the myelin concentration is multiplied by its molar susceptibility. The myelin susceptibility distribution of NAWM in Mst is denoted as wMst. The myelin susceptibility distribution in Mt2 is denoted as mMt2. A clustering analysis is performed to partition Mt2 into a hyperintense subregion denoted as M+ with a myelin susceptibility distribution sM+, an isointense subregion denoted as M0 with a myelin susceptibility distribution sM0, and a hypointense subregion denoted as M− with a myelin susceptibility distribution sM−.

In some implementations, the clustering analysis is executed using a distribution-based clustering analysis, including simple rectangular distribution, which is thresholding. In an exemplary implementation, wMst, sM+, sM0 and sM− are modeled as rectangular distributions in the myelin susceptibility value space or bins in the myelin susceptibility histogram domain. Then sM+ corresponds to the bin with myelin susceptibility values above the bin defined by wMst, sM0 corresponds to the bin defined by wMst, and sM− corresponds to the bin below the bin defined by wMst. The width of sM+ and sM− can be adjusted to accommodate all points above and below the wMst bin.

In another exemplary implementation, wMst, sM+, sM0 and sM− are modeled as Gaussian distributions in the myelin susceptibility value space. Then the mean of sM+ is higher than the mean of wMst, the mean and standard deviation of sM0 are the same as that of wMst, and the mean of sM− is lower than the mean of wMst. The standard deviations of sM+ and sM0 can be adjusted to provide optimal accommodation of all points using the expectation-maximization (EM) algorithm. The EM iterative algorithm can be applied here comprises the following steps: 1. Initialize estimates for parameters of means and variances for sM+ and sM−. 2. (Expectation) Compute the likelihood weights for each voxel myelin susceptibility value in Mst. 3. (Maximization). Update the estimates for the parameters using the maximum likelihood estimator formula. 4. Repeat steps 2 and 3 until reaching a convergency limit.

Then sM0 and sM− are used to monitor remyelination in multiple sclerosis. Remyelination may occur in response to therapy. The number of voxels in M0 and M−, the mean of sM−, and the product of the number of voxel in M− and the mean of sM− representing a magnetic moment, as well as other measures generated from sM0 and sM−, can be used to characterize the degree of remyelination.

3 Device System Implementation

Figure 5A:
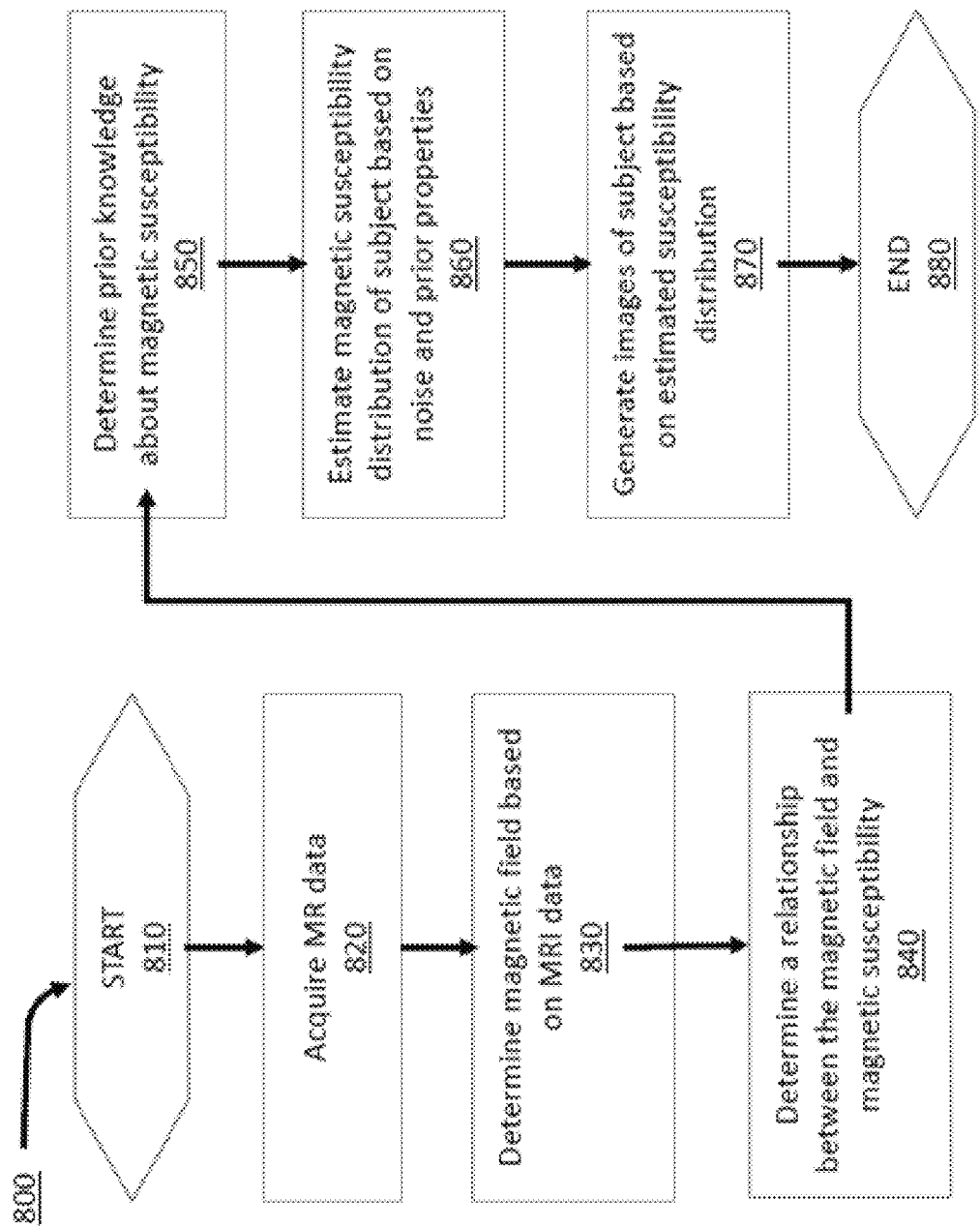
FIGS. 5A-5B show example processes for mapping tissue magnetic susceptibility A) using the magnetic field estimation and B) without using the magnetic field estimation.
Figure 5B:
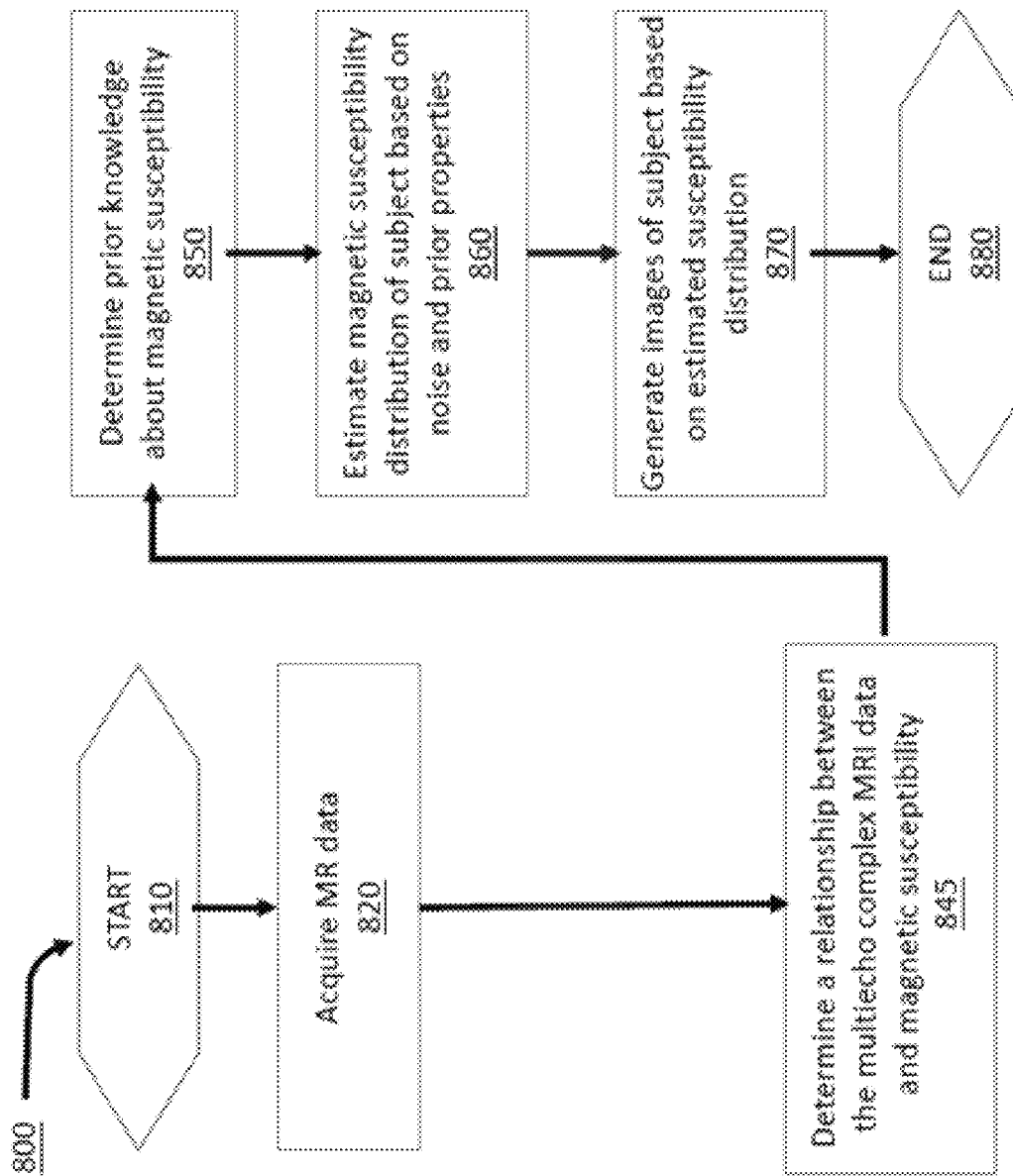

In some cases, one or more of the above quantitative susceptibility mapping techniques can be implemented using the process 800 shown in FIGS. 5A-5B. As an example, the process 800 can be used to map the tissue magnetic susceptibility of a subject, such as a patient (or portion of a patient) or an experimental sample (e.g., an imaging phantom, a sample of material or tissue, and so forth).

In some implementations, the process 800 can be used to transform MRI signal data corresponding to a subject into susceptibility-based images that quantitatively depict the structure and/or composition of the subject. As an example, in some cases, the process 800 can be used to obtain MRI data corresponding a subject, and process this MR data to generate a quantitative susceptibility map of the subject. Using this quantitative susceptibility map, one or more susceptibility-based images of the subject can be generated and displayed to a user. The user can then use these images for diagnostic or experimental purposes, for example to investigate the structure and/or composition and/or function of the subject, and/or to diagnose various conditions or diseases based, and/or to treat various conditions or diseases based, at least in part, on the images. As the process 800 can result in susceptibility-based images having higher quality and/or accuracy compared to other susceptibility mapping techniques, implementations of the process 800 can be used to improve a user's understanding of a subject's structure and/or composition and/or function, and can be used to improve the accuracy of any resulting medical diagnoses or experimental analyses.

The process 800 begins by acquiring magnetic resonance (MR) data corresponding to a subject (step 810). In some cases, the MR data can correspond to a patient (e.g., the entirety of a patient or a portion of a patient, such as a particular portion to the patient's body). In some cases, the MR data can correspond to one or more samples (e.g., an imaging phantom, a sample of one or more materials, a sample of one or more types of tissue, and/or one or more other objects).

In some implementations, the MR data can be acquired using an MRI scanner using one or more suitable pulse sequences. As an example, in some cases, MR data can be acquired using a gradient echo sequence that acquires MR data at a single echo time or at multiple echo times (e.g., two, three, four, five, and so forth). Various scan parameters can be used. As another example, MR data can be obtained using a 3D multiecho spoiled gradient echo sequence on a 3T scanner using a pulse sequence that samples at different echo times (TE) (e.g., 4 TEs, such as 3.8, 4.3, 6.3 and 16.3 ms) in an interleaved manner, and with following imaging parameters: repetition time (TR)=22 ms; voxel size=. 5×0.5×0.5 mm3, matrix size=256×64×64; bandwidth (BW)=±31.25 kHz; flip angle=15°. As another example, MR data can be obtained using a 3D multi-gradient echo sequence on a 3T scanner using imaging parameters TE/$\Delta$TE/#TE/TR/FA/BW/FOV/matrix size=5 ms/5 ms/8/50 ms/20°/±62.50 kHz/21.8×24×12.8 cm$^3$/232×256×64. Although an example sequences and example parameters are described above, these are merely illustrative. In practice, other sequences and parameters can be used, depending on various factors (e.g., the size of region to be examined, a known or assumed range of susceptibility values of the subject, scan time considerations, device limitations, and so forth).

After acquiring MR data corresponding to a subject, the process 800 continues by determining a magnetic field based on the MR data (step 820). As noted above, in some cases, the MRI signal phase is affected by the magnetic field corresponding to the magnetic susceptibility distribution of the subject and the chemical shift of tissue components.

In some implementations as illustrated in FIG. 5A, the magnetic field can be determined from the complex MR data by fitting the detected signal as a sum over tissue spectral components, where each component signal characterized by an exponent with a negative real part representing signal decay and an imaginary part representing phase dependent on the magnetic field and the chemical shift (step 830). This fitting for such a complex signal model can be performed iteratively using numerical optimization. A robust initialization for numerical optimization may be estimated using deep neural network. After determining the magnetic field based on the MR data, the process 800 continues by determining a relationship between the magnetic field and magnetic susceptibility (step 840). As described above, in some implementations, the relationship between the magnetic field and magnetic susceptibility can be expressed as a relationship between the magnetic field distribution in space to the magnetic susceptibility at a given location.

In some implementations as illustrated in FIG. 5B, the magnetic field estimation step is bypassed, and the estimation of magnetic susceptibility map is performed directly on the multiecho complex data by forming a relationship between the multiecho complex data and the magnetic susceptibility (step 845).

Then process 800 continues by determining prior knowledge about tissue magnetic susceptibility distribution (step 850). One estimation of tissue susceptibility distribution is to use R2* values derived from the magnitude signal. High R2* values can be used to identify high susceptibility regions such as hemorrhages for preconditioning to accelerate the convergence of numerical optimization. An example of preconditioning is to separate the whole image volume into region with high susceptibility (including hemorrhages, air regions and background) and region with normal tissue susceptibility. The low (near zero) R2* regions can also be used for identifying regions of low susceptibility contrasts such as cerebrospinal fluid in the ventricles in the brain. As these regions have known susceptibility values, they can be used to serve zero references (to water) to generate absolute susceptibility values using a minimal variance regularization and to suppress streaking and shadowing artifacts.

After obtaining the susceptibility prior information and signal data noise property, the process 800 continues by estimating a magnetic susceptibility distribution of the subject based, at least in part, on the prior information and data noise property (step 860). As described above, estimating the susceptibility distribution of the subject can include determining a cost function corresponding to a susceptibility distribution, the magnetic field or the multiecho complex data, masks corresponding to regions of interest. The cost function in some includes a data fidelity term based on data noise property expressing the relationship between tissue susceptibility and the magnetic field in an integral or differential form or expressing the relationships between tissue susceptibility and the multiecho complex data, and a regularization term expressing prior information. The estimated susceptibility distribution of the subject can be determined by identifying a particular susceptibility distribution that minimizes one or more of these cost functions described above, in some cases, this can be determined numerically.

After estimating a magnetic susceptibility distribution of the subject, the process 800 continues by generating one or more images of the subject based on the estimated susceptibility distribution of the subject (step 870). These images can be electronically displayed on a suitable display device (e.g., a liquid crystal display (LCD) display device, light-emitting diode (LED) display device, cathode-ray tube (CRT) display device, or other display device that can be configured to show images) and/or physically displayed on a suitable medium (e.g., printed, etched, painted, imprinted, or otherwise physically presented on a sheet or paper, plastic, or other material).

In some cases, the estimated susceptibility distribution of the subject can be visualized using a color scale, where each of several colors is mapped to a particular susceptibility value or range of susceptibility values. Accordingly, a two dimensional or three dimension image can be generated, where each pixel or voxel of the image corresponds to a particular spatial location of the subject, and the color of that pixel of voxel depicts the susceptibility value of the subject at that location.

In some cases, the color scale can include a gradient of colors and/or a gradient of gray shades (e.g., a gray scale), in order to depict a range of susceptibility values. In some cases, for a color scale that includes a gradient of colors or a gradient of gray shades, one end of the gradient can correspond to the lowest susceptibility value in a particular window of susceptibility values (e.g., an arbitrarily selected window of values), and the other end of the gradient can correspond to the highest susceptibility value in the window of values. For instance, for gray scale that includes a gradient of gray shades between pure white and pure black, pure white can be used to indicate the highest susceptibility value in a particular arbitrary window of values, and pure black can be used to indicate the lowest susceptibility value in the window of values. Other relationships between a color/gray scale and susceptibility values is also possible. For example, in some cases, for gray scale that includes a gradient of gray shades between pure white and pure black, pure white can be used to indicate the lower susceptibility value in a particular arbitrary window of values, and pure black can be used to indicate the highest susceptibility value in the window of values. Although the examples are described in the context of gray scales, in practice, similar relationships between color scales and susceptibility values are also possible.

Susceptibility values and colors can be mapped linearly (e.g., such that each absolute change in susceptibility value corresponds to a proportional change in color), logarithmically (e.g., such that each exponential change in susceptibility value correspond to a linear change in color), or according to any other mapping. Although examples mapping between color scales and susceptibility values are described above, these are merely illustrative examples. In practice, other mappings are also possible, depending on the implementation.

Figure 6:
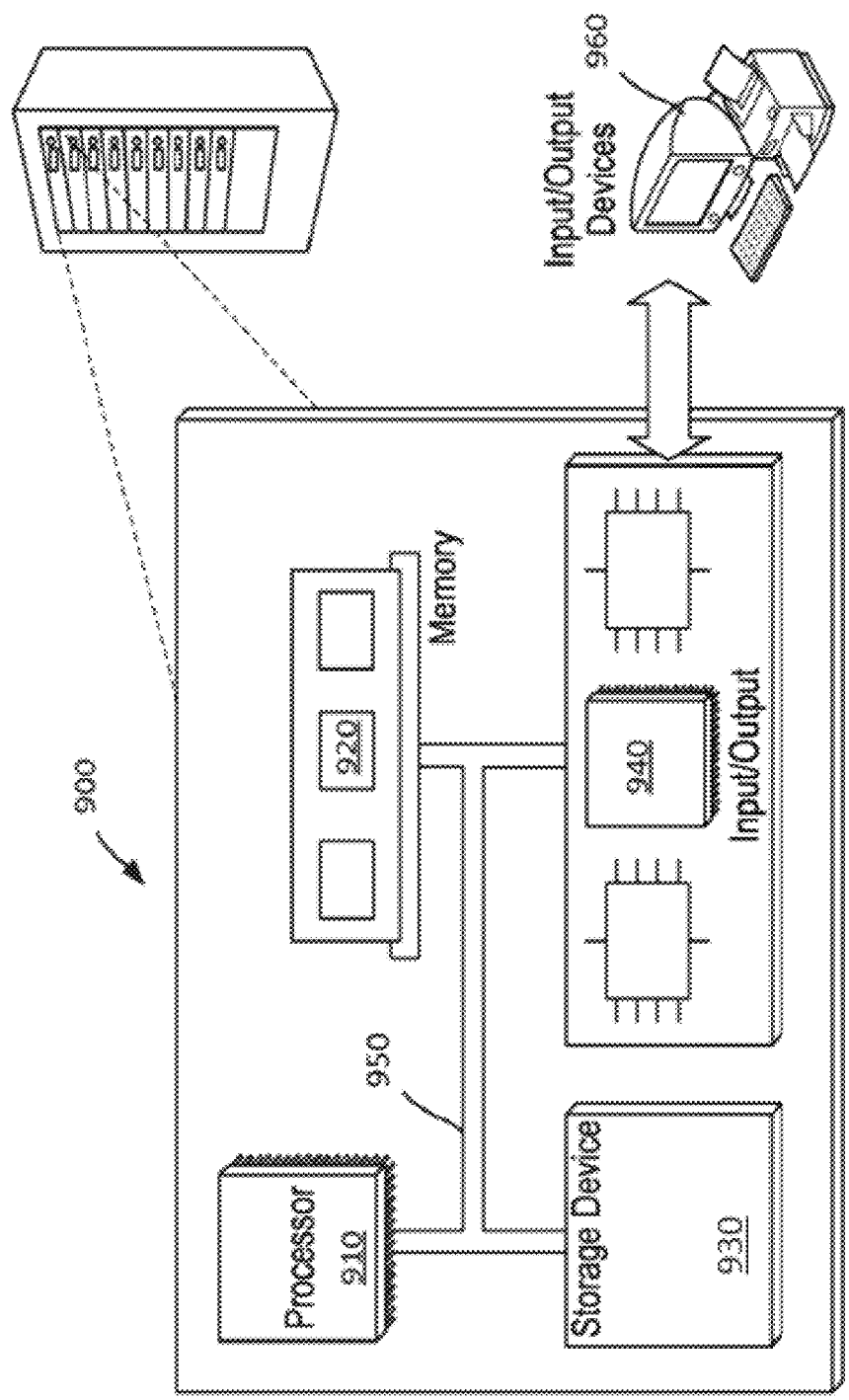
FIG. 6 is a block diagram of an example computer system.

Implementations of the above described techniques can be performed using a computer system. FIG. 6 is a block diagram of an example computer system 900 that can be used, for example, to perform implementations of the process 800. In some implementations, the computer system 900 can be communicatively connected to another computer system (e.g., another computer system 900), such that it receives data (e.g., MM datasets), and analyzes the received data using one or more of the techniques described above.

The system 900 includes a processor 910, a memory 920, a storage device 930, and an input/output device 940. Each of the components 910, 920, 930, and 940 can be interconnected, for example, using a system bus 950. The processor 910 is capable of processing instructions for execution within the system 900. In some implementations, the processor 910 is a single-threaded processor. In some implementations, the processor 910 is a multi-threaded processor. In some implementations, the processor 910 involves a graphic processing unit. In some implementations, the processor 910 is a quantum computer. The processor 910 is capable of processing instructions stored in the memory 920 or on the storage device 930. The processor 910 may execute operations such as performing one or more of the techniques described above.

The memory 920 stores information within the system 900. In some implementations, the memory 920 is a non-transitory computer-readable medium. In some implementations, the memory 920 is a volatile memory unit. In some implementations, the memory 920 is a non-volatile memory unit.

The storage device 930 is capable of providing mass storage for the system 900. In some implementations, the storage device 930 is a non-transitory computer-readable medium. In various different implementations, the storage device 930 can include, for example, a hard disk device, an optical disk device, a solid-state drive, a flash drive, magnetic tape, or some other large capacity storage device. In some implementations, the storage device 930 may be a cloud storage device, e.g., a logical storage device including multiple physical storage devices distributed on a network and accessed using a network. In some examples, the storage device may store long-term data. The input/output device 940 provides input/output operations for the system 900. In some implementations, the input/output device 940 can include one or more of network interface devices, e.g., an Ethernet card, a serial communication device, e.g., an RS-232 port, and/or a wireless interface device, e.g., an 802.11 card (e.g. 802.11ax), a 3G wireless modem, a 4G wireless modem, a 5G wireless modem, etc. A network interface device allows the system 900 to communicate, for example, transmit and receive data. In some implementations, the input/output device can include driver devices configured to receive input data and send output data to other input/output devices, e.g., a keyboard, a mouse, a printer, a sensor (e.g., a sensor that measures component or system-related properties, a sensor that measures environmental-related properties, or other types of sensors), and a display device 960. In some implementations, mobile computing devices, mobile communication devices, and other devices can be used.

A computing system can be realized by instructions that upon execution cause one or more processing devices to carry out the processes and functions described above, for example, storing, maintaining, and displaying information. Such instructions can include, for example, interpreted instructions such as script instructions, or executable code, or other instructions stored in a computer readable medium. A computing system can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

Although an example processing system has been described in FIG. 6, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as performing one or more of the above described processes, can be implemented as one or more computer program products, e.g., one or more modules of computer program instructions encoded on a tangible program carrier, for example a non-transitory computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "processing module" may encompass all apparatus, devices, and machines for processing data, including by way of example a programmable processor, a computer, or multiple processors or computers. A processing module can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., erasable programmable read-only memory (EPROM), electronically EPROM (EEPROM), and flash memory devices; magnetic disks, e.g., internal hard disks or removable disks or magnetic tapes; magneto optical disks; and compact disc-read only memory (CD-ROM) and digital video disc-read only memory (DVD-ROM) disks. The processor and the memory can be supplemented by, or incorporated in, special purpose logic circuitry. Sometimes a server is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

Figure 7A:
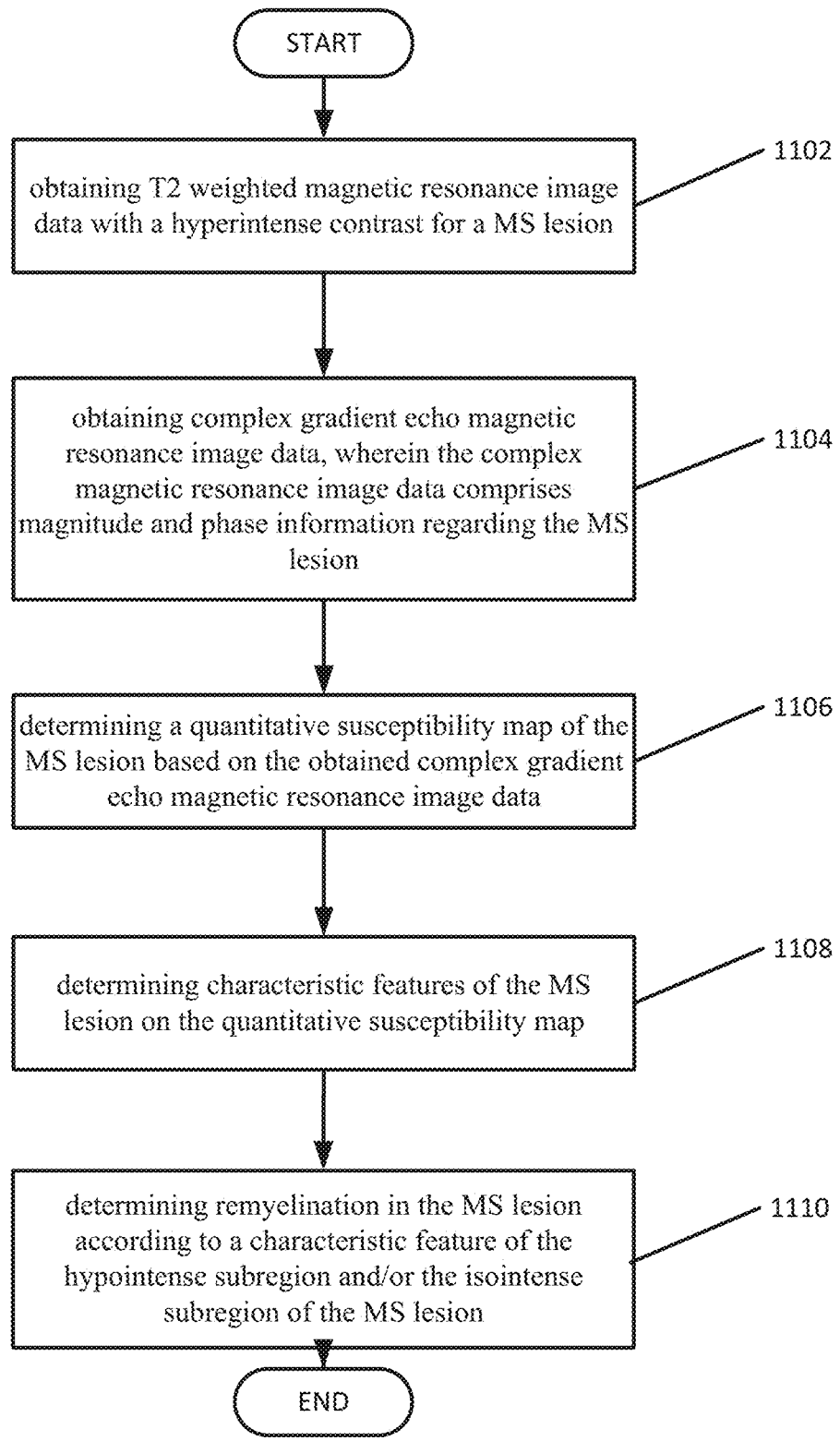
FIGS. 7A-7B show an exemplary process for monitoring remyelination in patients with multiple sclerosis (MS) using magnetic resonance imaging according to one embodiment of this disclosure.
Figure 7B:
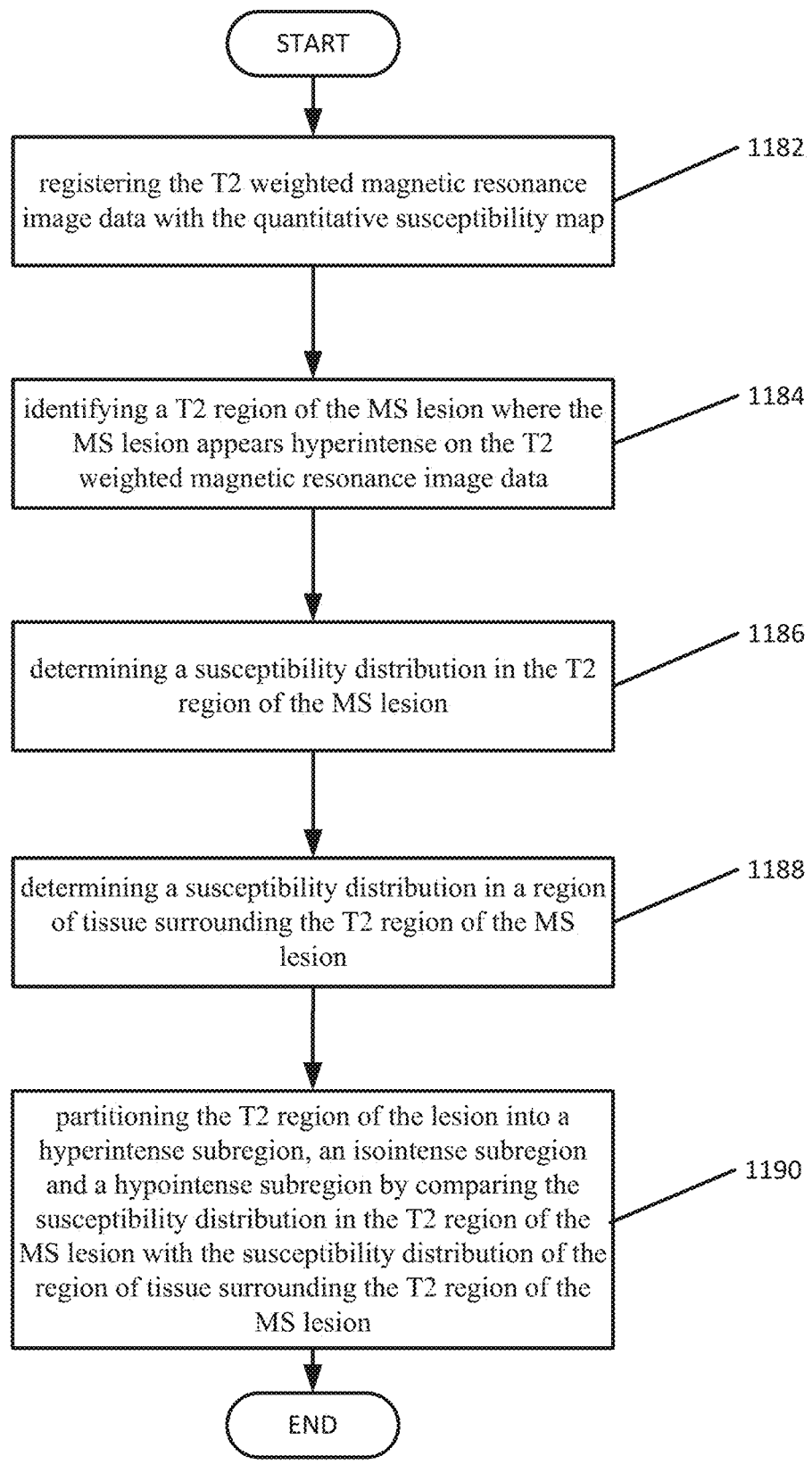

FIGS. 7A-7B show an exemplary process for monitoring remyelination in patients with multiple sclerosis (MS) using magnetic resonance imaging according to one embodiment of this disclosure. In particular, FIG. 7A depicts an exemplary method for monitoring remyelination in patients with multiple sclerosis (MS) using magnetic resonance imaging, wherein the method includes: at stage 1102, obtaining T2 weighted magnetic resonance image data with a hyperintense contrast for a MS lesion; at stage 1104, obtaining complex gradient echo magnetic resonance image data, wherein the complex magnetic resonance image data comprises magnitude and phase information regarding the MS lesion; at stage 1106, determining a quantitative susceptibility map of the MS lesion based on the obtained complex gradient echo magnetic resonance image data; at stage 1108, determining characteristic features of the MS lesion on the quantitative susceptibility map, and at stage 1110, determining remyelination in the MS lesion according to a characteristic feature of the hypointense subregion and/or the isointense subregion of the MS lesion.

FIG. 7B depicts exemplary details for determining the characteristic features of the MS lesion, including: at stage 1182, registering the T2 weighted magnetic resonance image data with the quantitative susceptibility map; at stage 1184, identifying a T2 region of the MS lesion where the MS lesion appears hyperintense based on the T2 weighted magnetic resonance image data; at stage 1186, determining a susceptibility distribution in the T2 region of the MS lesion; at stage 1188, determining a susceptibility distribution in a region of tissue surrounding the T2 region of the MS lesion; and at stage 1190, partitioning the T2 region of the lesion into a hyperintense subregion, an isointense subregion, and a hypointense subregion by comparing the susceptibility distribution in the T2 region of the MS lesion with the susceptibility distribution of the region of tissue surrounding the T2 region of the MS lesion.

Certain features that are described above in the context of separate implementations can also be implemented in combination in a single implementation. Conversely, features that are described in the context of a single implementation can be implemented in multiple implementations separately or in any sub-combinations.

The order in which operations are performed as described above can be altered. In certain circumstances, multitasking and parallel processing may be advantageous. The separation of system components in the implementations described above should not be understood as requiring such separation.

U.S. patent application Ser. No. 17/614,277, titled "System and Method of Perceptive Quantitative Mapping of Physical Properties," filed on Nov. 24, 2021 to Yi Wang et al., and U.S. Pat. No. 10,890,641, titled "System and Method of Robust Quantitative Susceptibility Mapping," to Yi Wang et al., issued on Jan. 12, 2021, are hereby incorporated by reference in their entireties.

A number of embodiments of the disclosure have been described. Nevertheless, it will be understood that various modifications may be made without departing from the spirit and scope of the disclosure. Accordingly, other embodiments are within the scope of the following claims.

The invention claimed is:

1. A method for monitoring remyelination in patients with multiple sclerosis (MS) using magnetic resonance imaging, the method comprising:
receiving, by a computer system comprising a processing device, T2 weighted magnetic resonance image data and complex gradient echo magnetic resonance image data from a magnetic resonance scanner, the T2 weighted magnetic resonance image data comprising a hyperintense contrast for a MS lesion, and the complex gradient echo magnetic resonance image data comprising magnitude and phase information regarding the MS lesion;
determining, using the processing device, a quantitative susceptibility map of the MS lesion based on the received complex gradient echo magnetic resonance image data;
determining, using the processing device, characteristic features of the MS lesion on the quantitative susceptibility map, wherein determining the characteristic features comprises:
registering, using the processing device, the received T2 weighted magnetic resonance image data with the quantitative susceptibility map;
identifying, using the processing device, a T2 region of the MS lesion where the MS lesion appears hyperintense based on the received T2 weighted magnetic resonance image data;
determining, using the processing device, a susceptibility distribution in the T2 region of the MS lesion;
determining, using the processing device, a susceptibility distribution in a region of tissue surrounding the T2 region of the MS lesion; and
partitioning, using the processing device, the T2 region of the MS lesion into a hyperintense subregion, an isointense subregion, and a hypointense subregion by comparing the susceptibility distribution in the T2 region of the MS lesion with the susceptibility distribution of the region of tissue surrounding the T2 region of the MS lesion, wherein the partitioning is based on a distribution-based clustering; and
determining, using the processing device, remyelination in the MS lesion according to a characteristic feature of the hypointense subregion and/or the isointense subregion of the MS lesion.

2. The method of claim 1, wherein comparing the susceptibility distribution in the T2 region of the MS lesion with the susceptibility distribution of the region of tissue surrounding the T2 region of the MS lesion comprises measuring susceptibility values on the quantitative susceptibility map.

3. The method of claim 1, wherein determining the quantitative susceptibility map comprises using the phase information and additional information.

4. A method for monitoring remyelination in patients with multiple sclerosis (MS) using magnetic resonance imaging, the method comprising:
receiving, by a computer system comprising a processing device, T2 weighted magnetic resonance image data and complex gradient echo magnetic resonance image data from a magnetic resonance scanner, the T2 weighted magnetic resonance image data comprising a hyperintense contrast for a MS lesion, and the complex gradient echo magnetic resonance image data comprising magnitude and phase information regarding the MS lesion;
determining, using the processing device, a quantitative susceptibility map of the MS lesion based on the received complex gradient echo magnetic resonance image data;
determining, using the processing device, characteristic features of the MS lesion on the quantitative susceptibility map, wherein determining the characteristic features comprises:
registering, using the processing device, the received T2 weighted magnetic resonance image data with the quantitative susceptibility map;

identifying, using the processing device, a T2 region of the MS lesion where the MS lesion appears hyperintense based on the received T2 weighted magnetic resonance image data;
determining, using the processing device, a susceptibility distribution in the T2 region of the MS lesion;
determining, using the processing device, a susceptibility distribution in a region of tissue surrounding the T2 region of the MS lesion; and
partitioning, using the processing device, the T2 region of the MS lesion into a hyperintense subregion, an isointense subregion, and a hypointense subregion by comparing the susceptibility distribution in the T2 region of the MS lesion with the susceptibility distribution of the region of tissue surrounding the T2 region of the MS lesion; and
determining, using the processing device, remyelination in the MS lesion according to a characteristic feature of the hypointense subregion and/or the isointense subregion of the MS lesion;
wherein determining the quantitative susceptibility map comprises identifying the region of tissue, wherein the region of tissue has an approximately uniform susceptibility, and enforcing a known uniform susceptibility value in the region of tissue.

5. The method of claim 1, wherein determining the quantitative susceptibility map comprises using a data fidelity term associated with a likelihood function associated with Gaussian noise.

6. The method of claim 1, wherein determining the characteristic features comprises using a susceptibility value measured on the quantitative susceptibility map.

7. The method of claim 1, wherein determining the characteristic features comprises using multiple parameters determined from magnetic resonance imaging.

8. The method of claim 1, wherein determining the characteristic features comprises calculating a R2* map from the complex gradient echo magnetic resonance image data and determining a myelin quantity from the R2* map and quantitative susceptibility map according to a calibrated curve.

9. The method of claim 1, wherein the region of tissue surrounding the T2 region of the MS lesion comprises a layer of normal appearing white matter and/or gray matter surrounding the MS lesion.

10. A computer system for generating one or more images of an object, the computer system comprising:
a processing device; and
a non-transitory computer storage medium having instructions stored thereon;
wherein the processing device is configured to execute the instructions to facilitate the following operations being performed by the computer system:
receiving T2 weighted magnetic resonance image data and complex gradient echo magnetic resonance image data from a magnetic resonance scanner, the T2 weighted magnetic resonance image data comprising a hyperintense contrast for a MS lesion, and the complex gradient echo magnetic resonance image data comprising magnitude and phase information regarding the MS lesion;
determining a quantitative susceptibility map of the MS lesion based on the received complex gradient echo magnetic resonance image data;
determining characteristic features of the MS lesion on the quantitative susceptibility map, wherein determining the characteristic features comprises:
registering the T2 weighted magnetic resonance image data with the quantitative susceptibility map;
identifying a T2 region of the MS lesion where the MS lesion appears hyperintense on the T2 weighted magnetic resonance image data;
determining a susceptibility distribution in the T2 region of the MS lesion;
determining a susceptibility distribution in a region of tissue surrounding the T2 region of the MS lesion; and
partitioning the T2 region of the MS lesion into a hyperintense subregion, an isointense subregion, and a hypointense subregion by comparing the susceptibility distribution in the T2 region of the MS lesion with the susceptibility distribution of the region of tissue surrounding the T2 region of the MS lesion; and
determining remyelination in the MS lesion according to a characteristic feature of the hypointense subregion and/or the isointense subregion of the MS lesion;
wherein determining the quantitative susceptibility map comprises identifying the region of tissue, wherein the region of tissue has an approximately uniform susceptibility, and enforcing a known uniform susceptibility value in the region of tissue.

11. The computer system of claim 10, wherein the partitioning is based on a distribution-based clustering.

12. The computer system of claim 10, wherein comparing the susceptibility distribution in the T2 region of the MS lesion with the susceptibility distribution of the region of tissue surrounding the T2 region of the MS lesion comprises measuring susceptibility values on the quantitative susceptibility map.

13. The computer system of claim 10, wherein determining the quantitative susceptibility map comprises using the phase information and additional information.

14. The computer system of claim 10, wherein determining the quantitative susceptibility map comprises using a data fidelity term associated with a likelihood function associated with Gaussian noise.

15. The computer system of claim 10, wherein determining the characteristic features comprises using a susceptibility value measured on the quantitative susceptibility map.

16. The computer system of claim 10, wherein determining the characteristic features comprises using multiple parameters determined from magnetic resonance imaging.

17. The computer system of claim 10, wherein determining the characteristic features comprises calculating a R2* map from the complex gradient echo magnetic resonance image data and determining a myelin quantity from the R2* map and quantitative susceptibility map according to a calibrated curve.

18. The computer system of claim 10, wherein the region of tissue surrounding the T2 region of the MS lesion comprises a layer of normal appearing white matter and/or gray matter surrounding the MS lesion.

19. The computer system of claim 10, wherein receiving the T2 weighted magnetic resonance image data and the complex gradient echo magnetic resonance image data from the magnetic resonance scanner comprises receiving the T2 weighted magnetic resonance image data and the complex gradient echo magnetic resonance image data from the magnetic resonance scanner via another computer system communicatively coupled to the computer system.

20. The method of claim 1, wherein the computer system receives the T2 weighted magnetic resonance image data and the complex gradient echo magnetic resonance image data from the magnetic resonance scanner via another computer system communicatively coupled to the computer system.

\* \* \* \* \*